United States Patent [19]
Tu et al.

[11] Patent Number: 5,938,923
[45] Date of Patent: Aug. 17, 1999

[54] MICROFABRICATED FILTER AND CAPSULE USING A SUBSTRATE SANDWICH

[75] Inventors: Jay Kuang-Jieh Tu, Berkeley; Mauro Ferrari, Lafayette, both of Calif.

[73] Assignee: The Regents of the University of California, Oakland, Calif.

[21] Appl. No.: 08/842,686

[22] Filed: Apr. 15, 1997

[51] Int. Cl.⁶ .......................... B01D 69/10; B01D 71/02; A61K 9/52
[52] U.S. Cl. .................. 210/490; 216/2; 216/56; 210/500.22; 210/500.26; 424/424; 424/451; 604/890.1
[58] Field of Search ................. 210/348, 321.6, 210/490, 488, 500.22, 500.26, 321.84, 500.25; 604/490.1, 491.1, 492.1; 424/423, 424, 451; 216/2, 56; 156/643, 645

[56] References Cited

U.S. PATENT DOCUMENTS

| | | | |
|---|---|---|---|
| 3,502,455 | 3/1970 | Gardner et al. | 65/31 |
| 3,791,987 | 2/1974 | Fanger | 252/316 |
| 3,936,329 | 2/1976 | Kendall et al. | 148/187 |
| 3,962,052 | 6/1976 | Abbas et al. | 204/129 |
| 4,063,271 | 12/1977 | Bean et al. | 357/49 |
| 4,077,885 | 3/1978 | van Heuven et al. | 210/193 |
| 4,473,476 | 9/1984 | Mc Millan et al. | 210/653 |
| 4,689,150 | 8/1987 | Abe et al. | 210/490 |
| 4,743,545 | 5/1988 | Torobin | 435/41 |
| 4,793,825 | 12/1988 | Benjamin et al. | 604/891 |
| 4,797,211 | 1/1989 | Enrfeld et al. | 210/500 |
| 4,874,484 | 10/1989 | Foell et al. | 204/129 |
| 4,978,421 | 12/1990 | Bassous et al. | 156/645 |
| 4,981,590 | 1/1991 | Van 'T Veen et al. | 210/490 |
| 5,131,978 | 7/1992 | O'Neill | 156/653 |
| 5,225,123 | 7/1993 | Torobin | 264/43 |
| 5,234,594 | 8/1993 | Tonucci et al. | 210/500 |
| 5,262,021 | 11/1993 | Lehmann et al. | 204/129 |
| 5,304,487 | 4/1994 | Wilding et al. | 210/500.26 |
| 5,393,375 | 2/1995 | MacDonald et al. | 156/643 |
| 5,543,046 | 8/1996 | Van Rijn | 210/490 |
| 5,585,011 | 12/1996 | Saaski et al. | 216/2 |
| 5,603,953 | 2/1997 | Herbing et al. | 424/473 |
| 5,651,900 | 7/1997 | Keller et al. | 210/490 |
| 5,770,076 | 6/1998 | Chu et al. | 210/490 |
| 5,792,354 | 8/1998 | Aksberg | 210/321.84 |
| 5,798,042 | 8/1998 | Chu et al. | 210/490 |

FOREIGN PATENT DOCUMENTS

| | | |
|---|---|---|
| 1680270 A1 | 9/1991 | U.S.S.R. . |
| WO 89/08489 | 9/1989 | WIPO . |
| WO 92/15408 | 9/1992 | WIPO . |
| WO 93/11862 | 6/1993 | WIPO . |

OTHER PUBLICATIONS

"Process for Producing a Precision Filter", IBM Technical Disclosure Bulletin, vol. 32, No. 4A Sep. 1989, Undated.

Bergqvist et al., "A New Condenser Microphone in Silicon", Sensors and Actuators, A21–A23, 1990, pp. 123–125.

Bourouina et al., "A new condenser microphone with a $p^+$ silicon membrane", Sensors and Actuators, Jan. 31, 1992, pp. 149–152.

E. Graf et al., "Silicon membrane condenser microphone with integrated field-effect transistor", Sensors and Actuators, 1993, pp. 708–711.

(List continued on next page.)

*Primary Examiner*—Joseph W. Drodge
*Attorney, Agent, or Firm*—Fish & Richardson P.C.

[57] ABSTRACT

A microfabricated filter made up of two bonded substrate structures, each consisting of single crystalline silicon can optionally be formed into a capsule. The pores of the filter consist of one or more channels disposed between the two substrate structures. The width of the channels are defined by a thickness of a sacrificial layer formed on one of the substrate structures. The filter includes pores having a precisely controlled pore width which may be as small as 5 nanometers. The filter provides a relatively high mechanical strength relative to filters having polycrystalline silicon structures and also has a high throughput and can be modified to have high resistance to adsorption of particles.

31 Claims, 15 Drawing Sheets

OTHER PUBLICATIONS

J.Brody, "A Planar Microfabricated Fluid Filter", 8th International Conference on Solid–State Sensors and Actuators, Jun. 25–29, 1995, pp. 779–782.

G.Kittilsland et al., "A Sub–micron Particle Filter in Silicon", Sensors and Actuators, 1990, pp. 904–907.

W.Lang et al., "Application of Porous Silicon as a Sacrificial Layer", 7th International Conference on Solid–State Sensors and Actuators Digest of Technical Papers, Jun. 7–10, 1993, pp. 202–205.

D.Pearson et al., "Nanochannel Glass Replica Membranes," Science, vol. 270, Oct. 6, 1995, pp. 68–69.

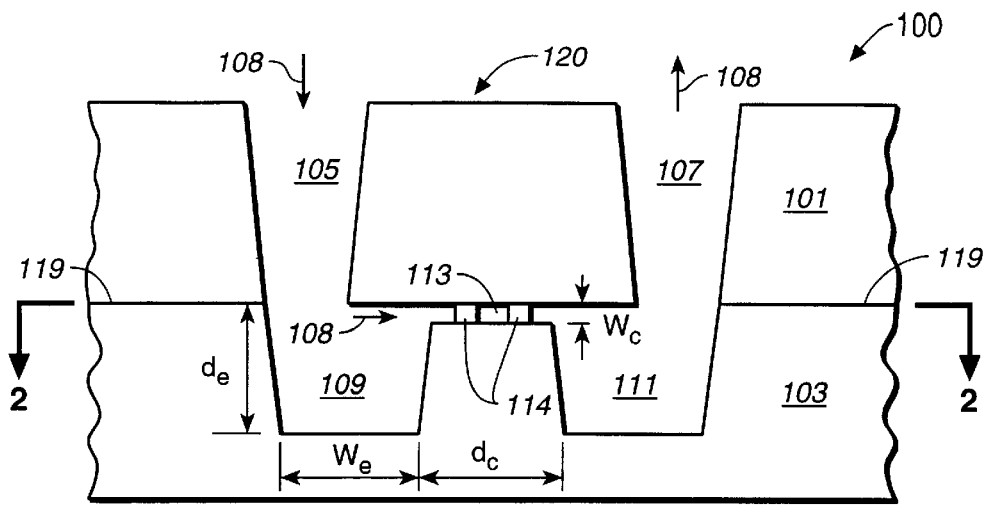
FIG._1
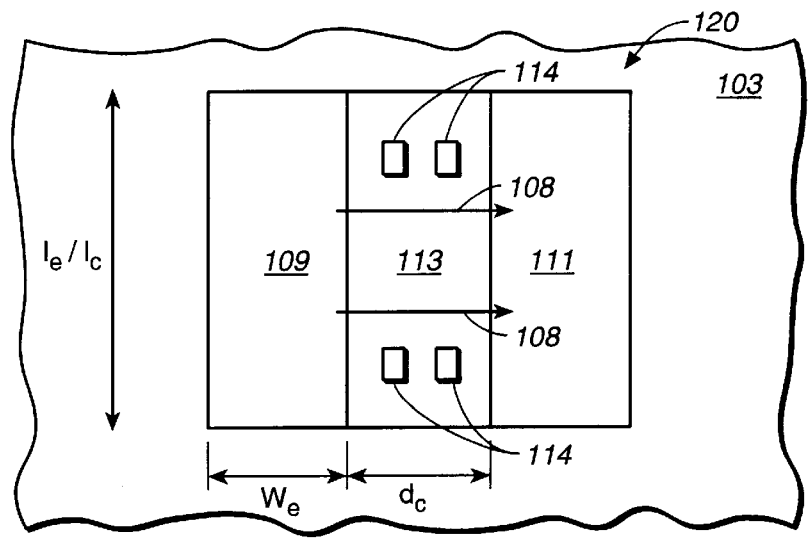
FIG._2
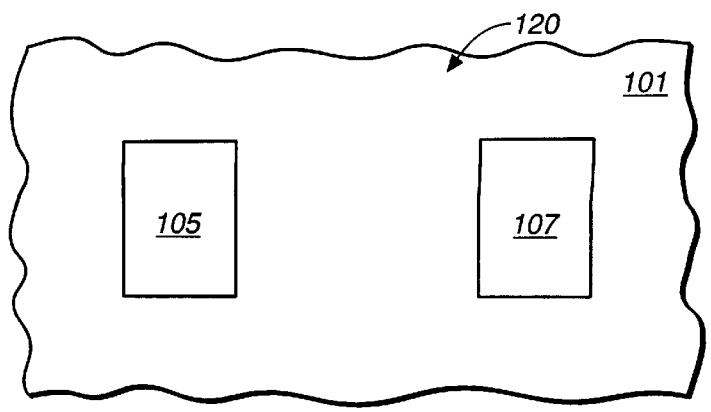
FIG._3

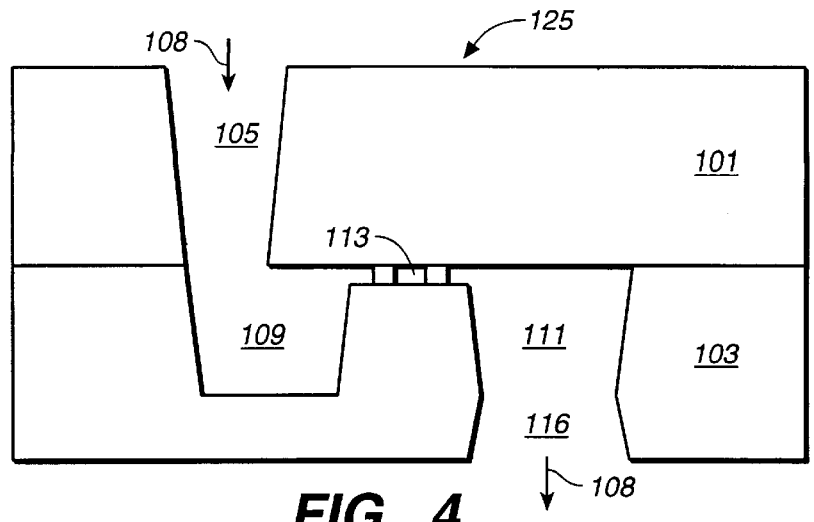
FIG._4
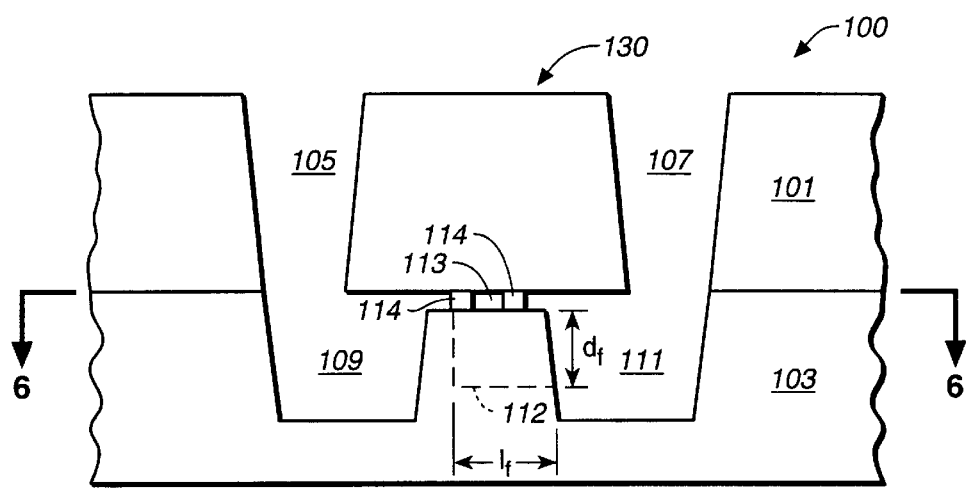
FIG._5
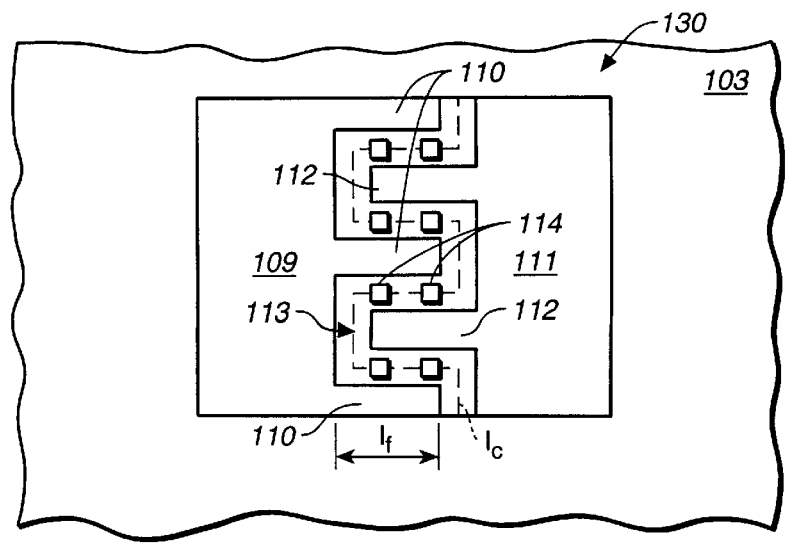
FIG._6A

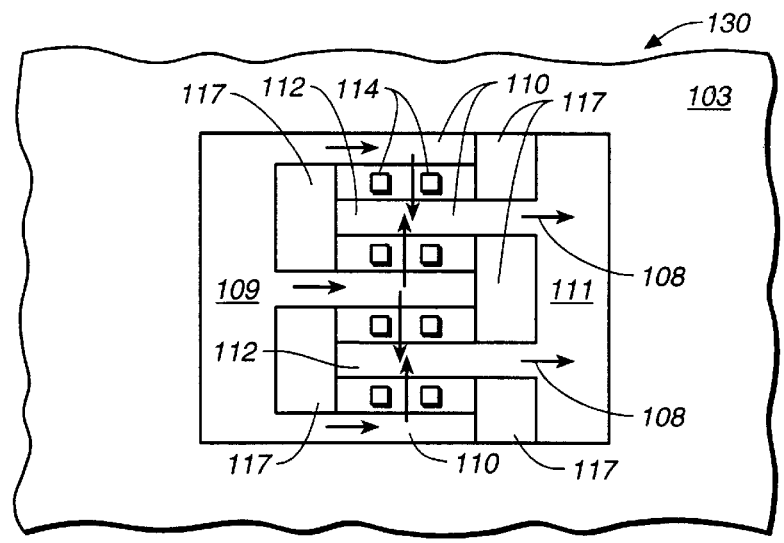
FIG._6B
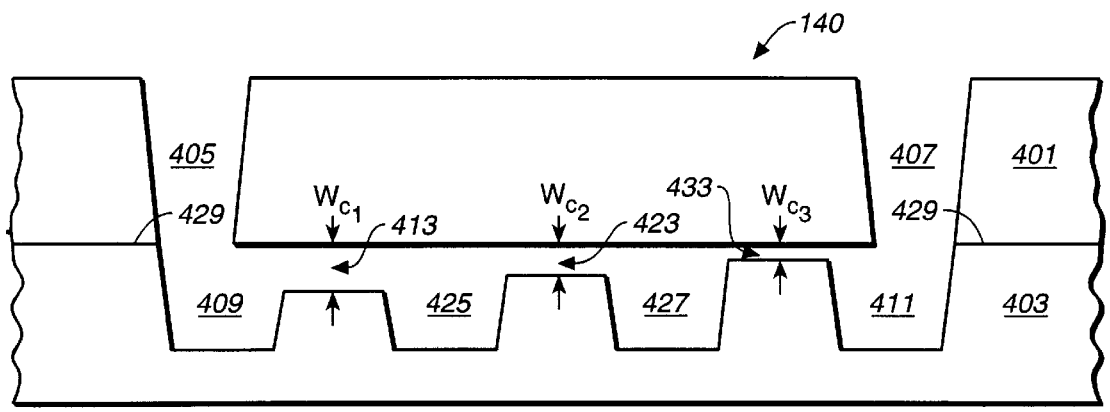
FIG._7
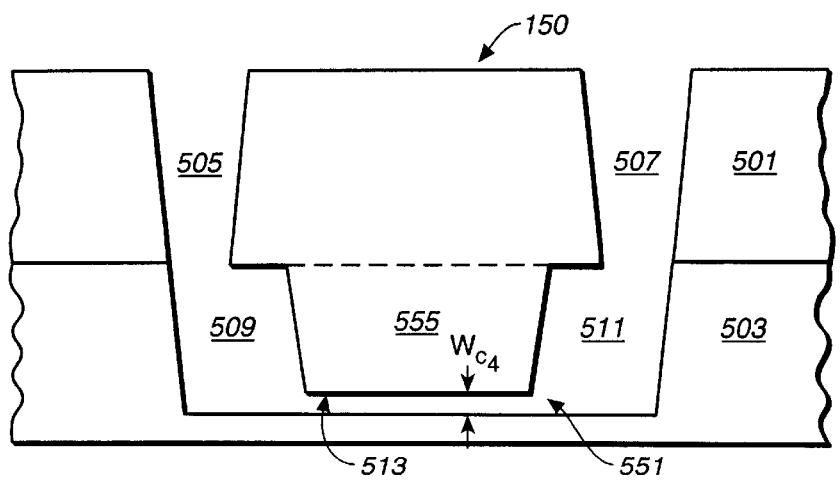
FIG._8

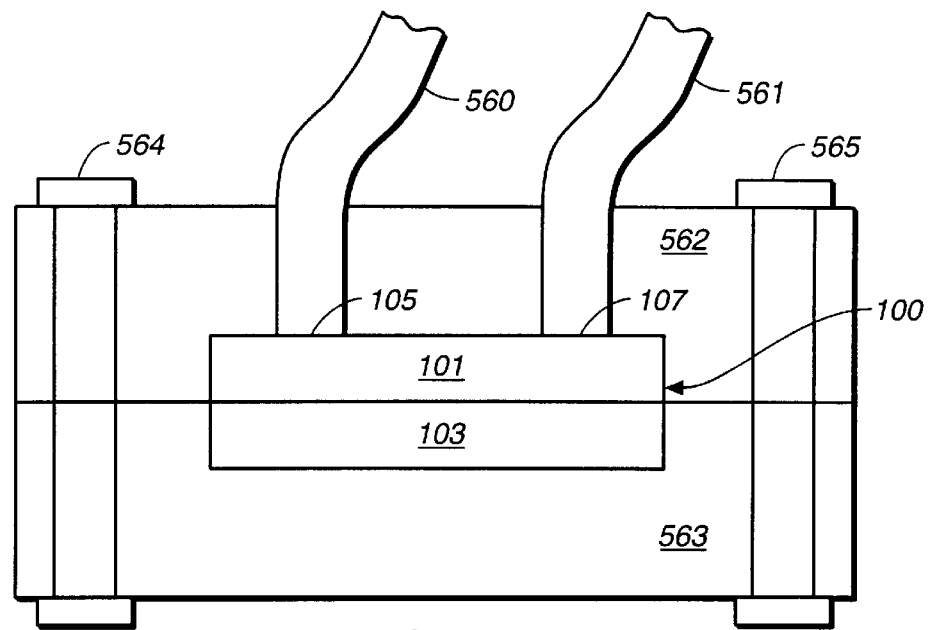
FIG._9
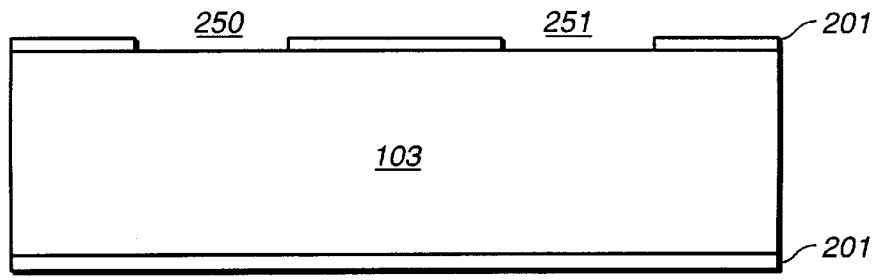
FIG._10
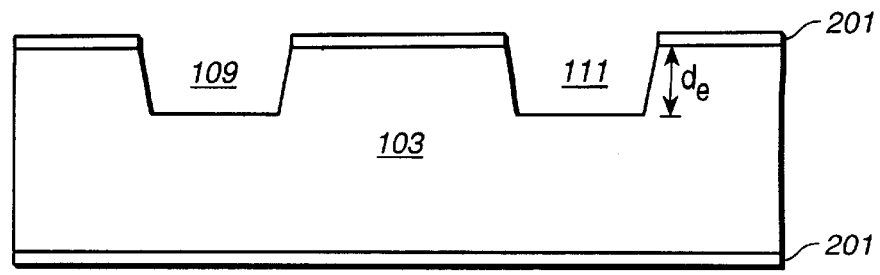
FIG._11

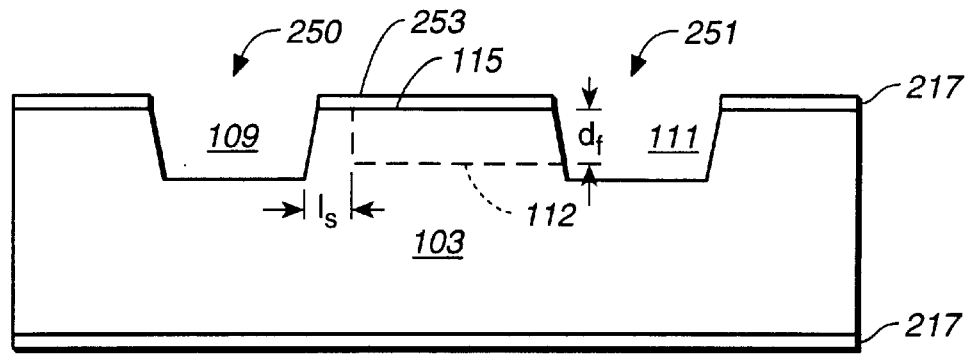
FIG._12
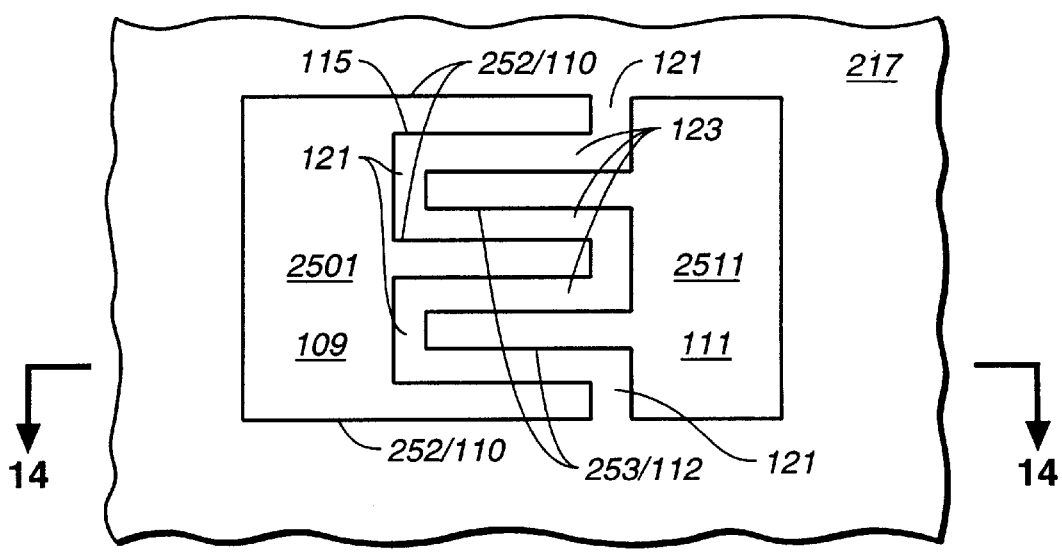
FIG._13
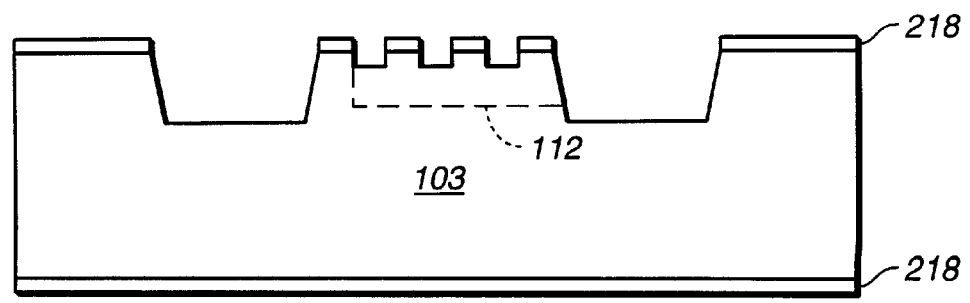
FIG._14

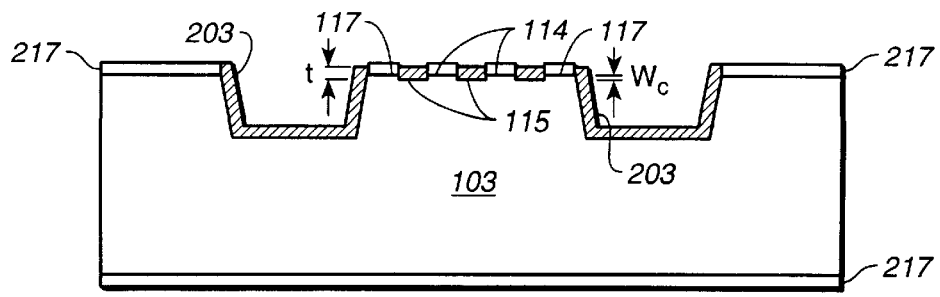
FIG._15
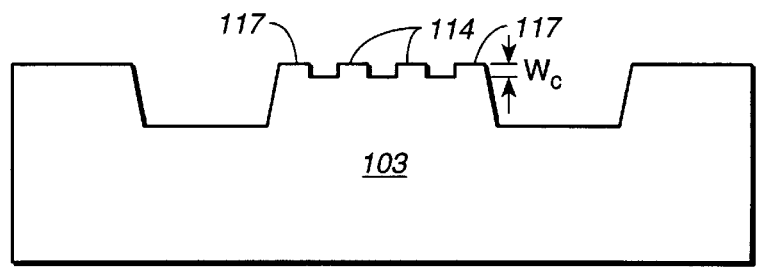
FIG._16
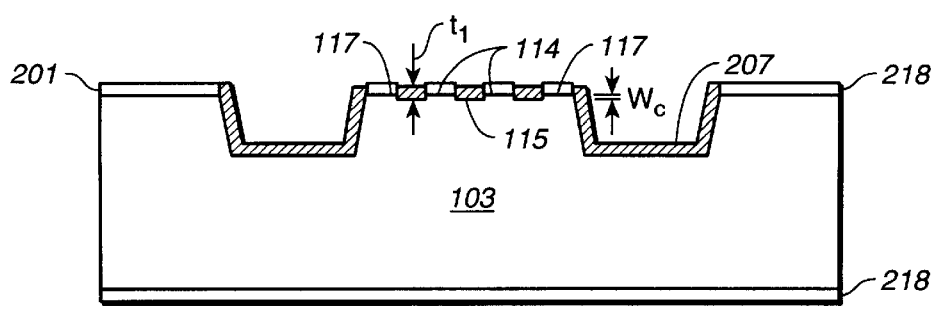
FIG._17
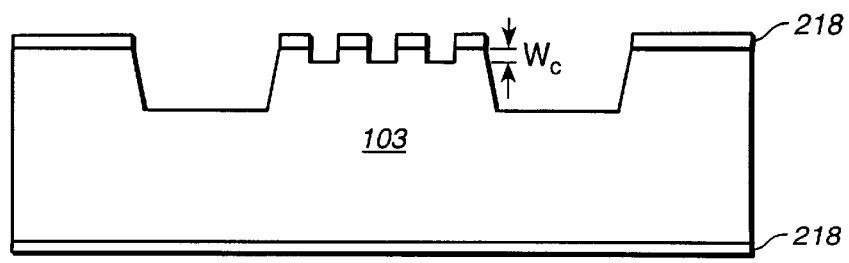
FIG._18

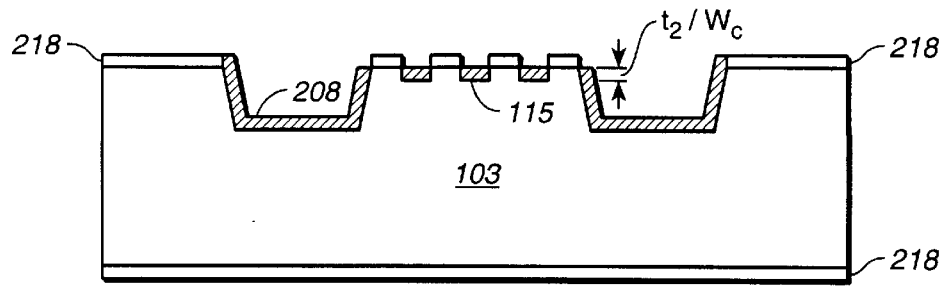
FIG._19
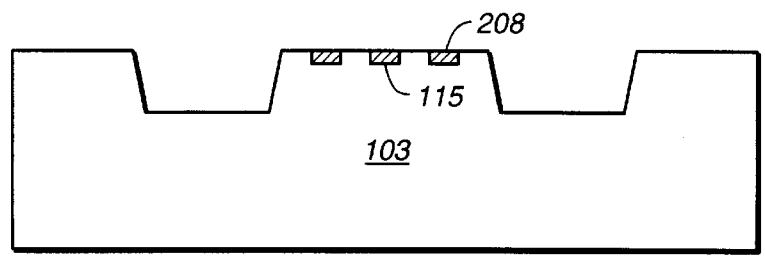
FIG._20
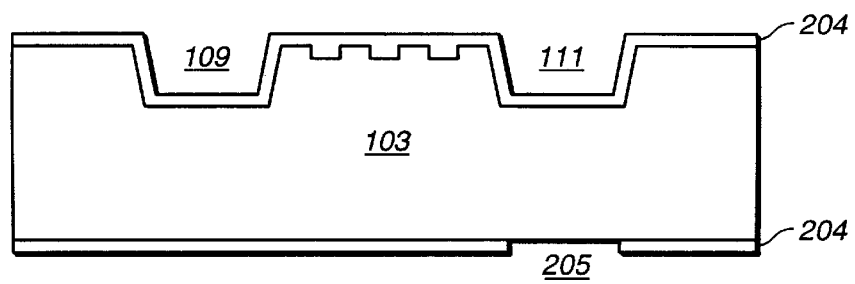
FIG._21
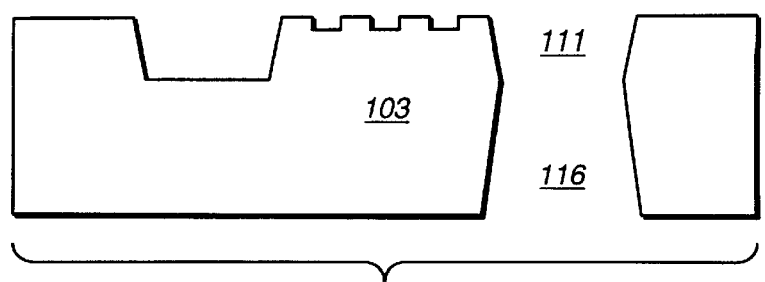
FIG._22

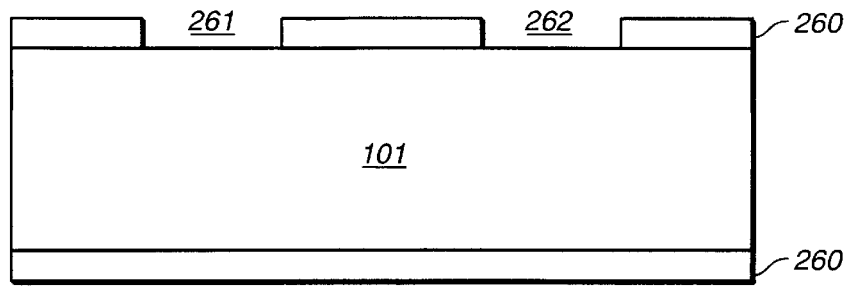
FIG._23
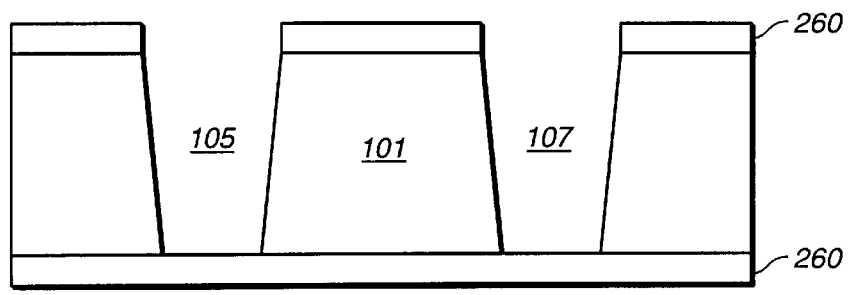
FIG._24
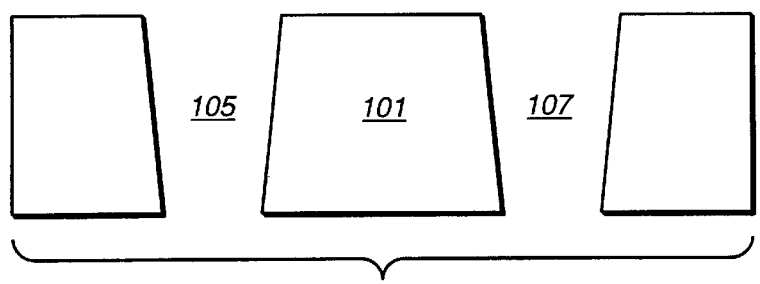
FIG._25
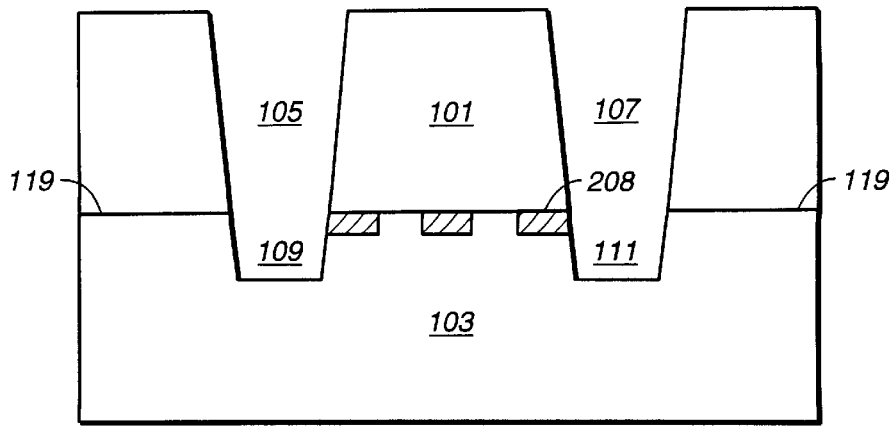
FIG._26

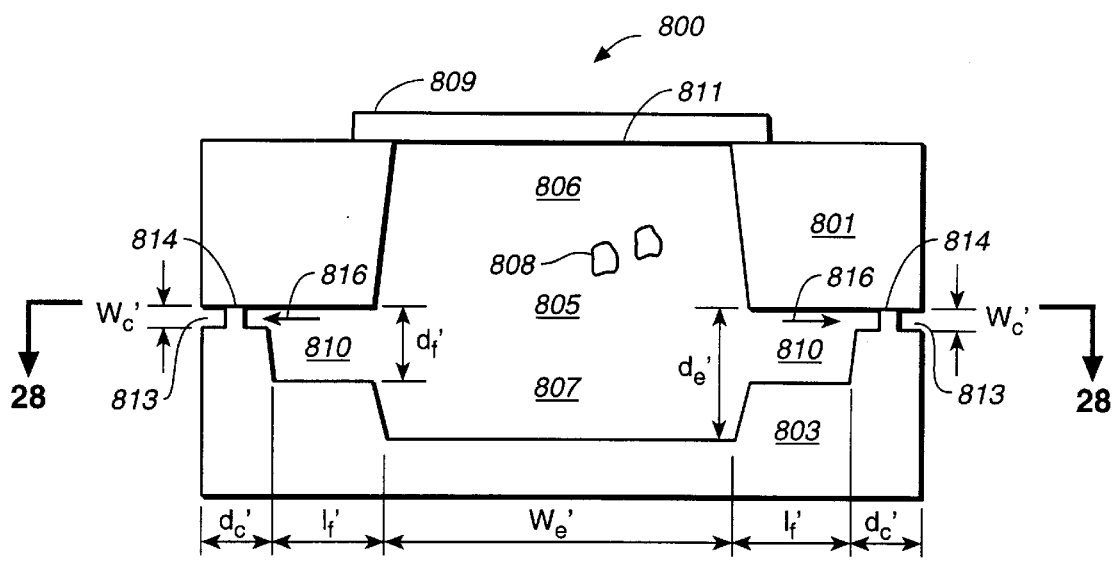
FIG._27
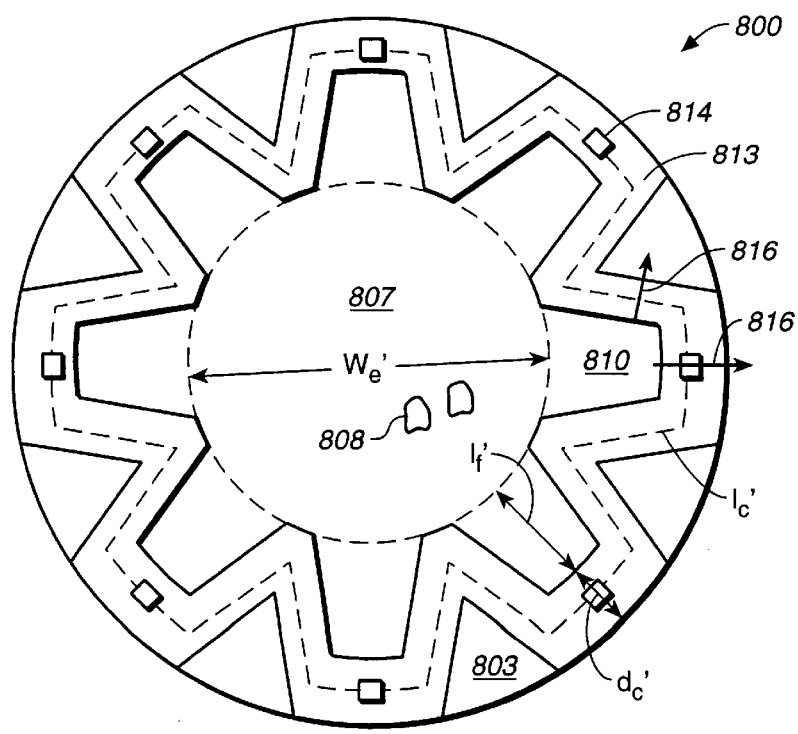
FIG._28

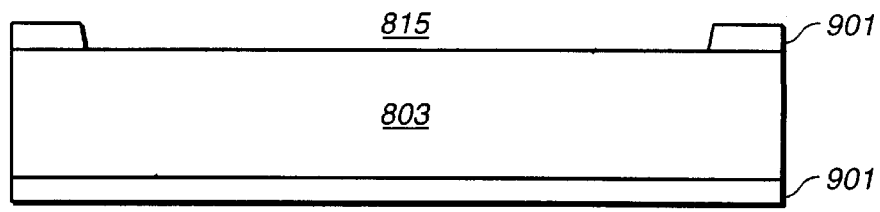
FIG._29
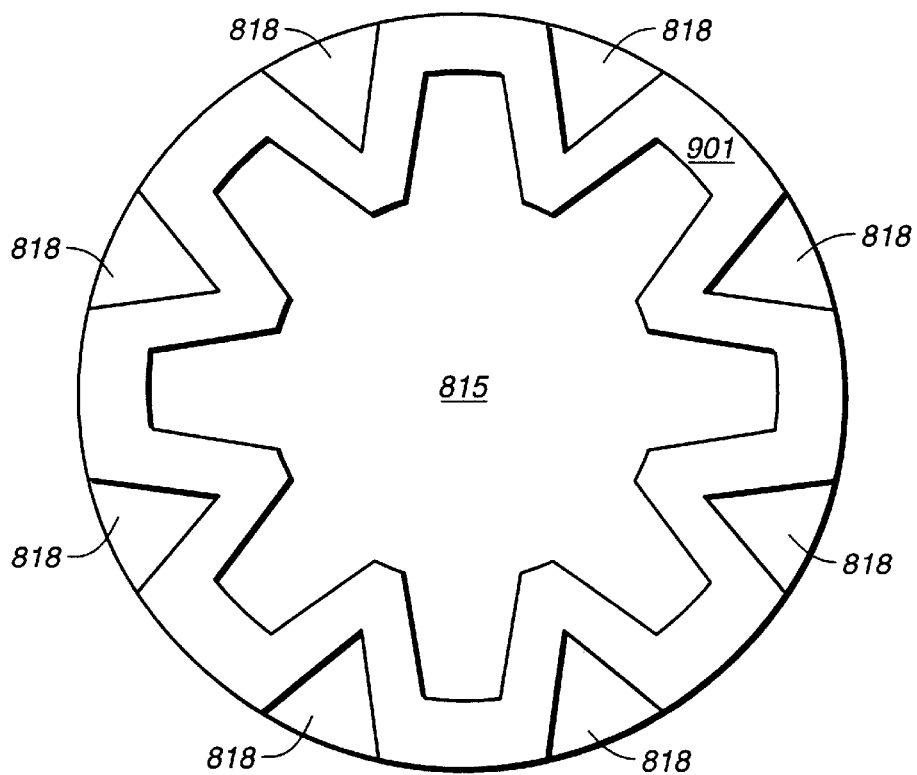
FIG._30
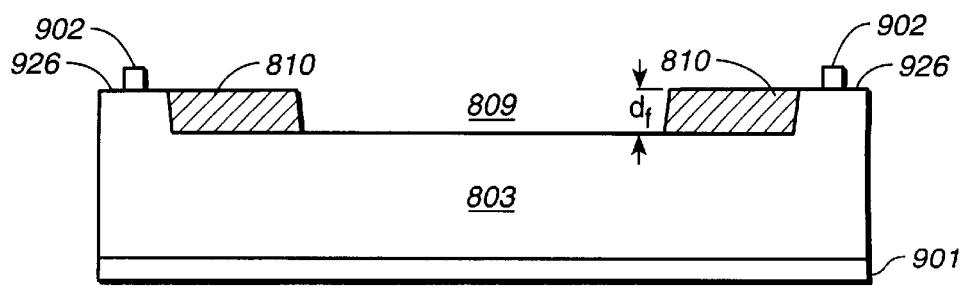
FIG._31

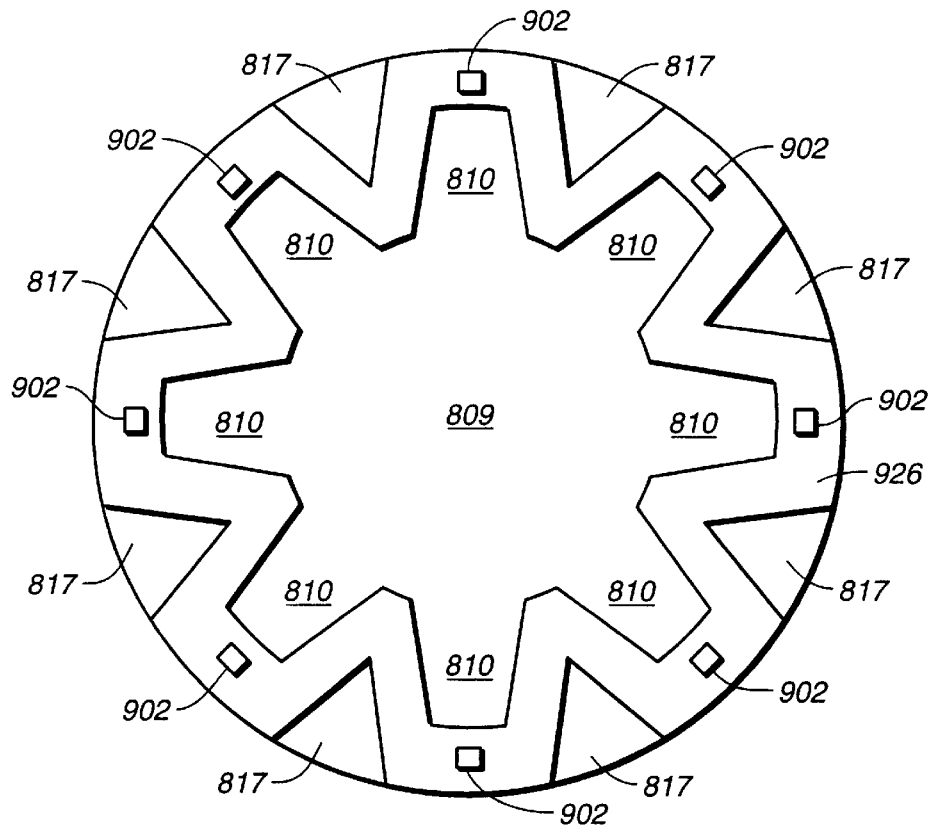
FIG._32
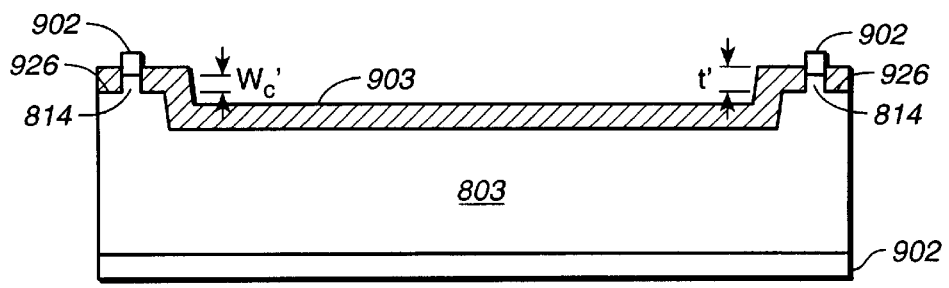
FIG._33
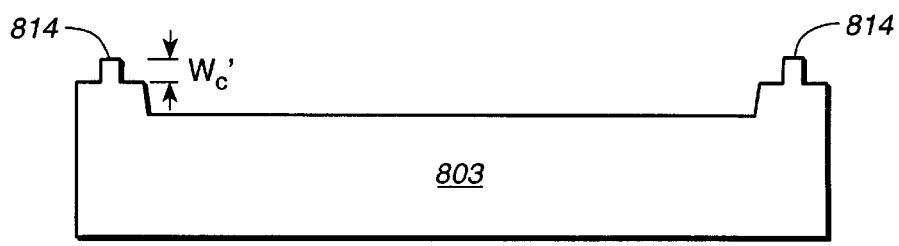
FIG._34

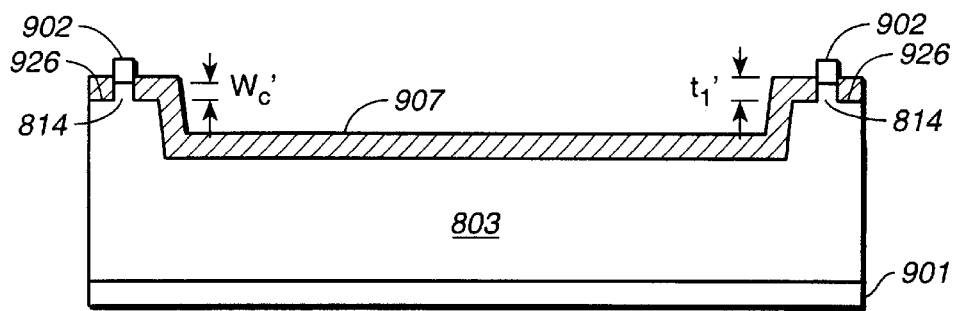
FIG._35
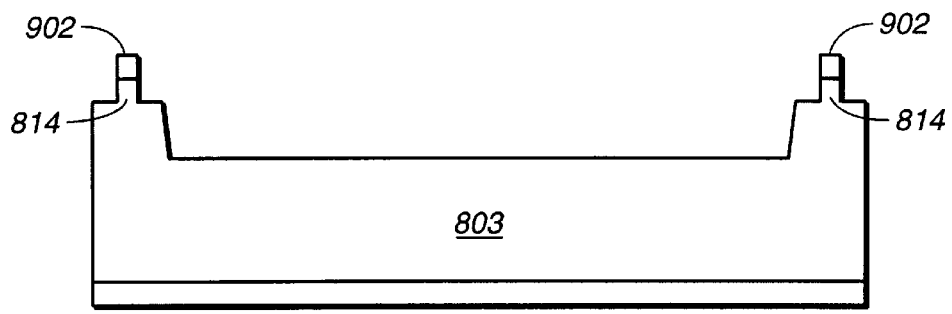
FIG._36
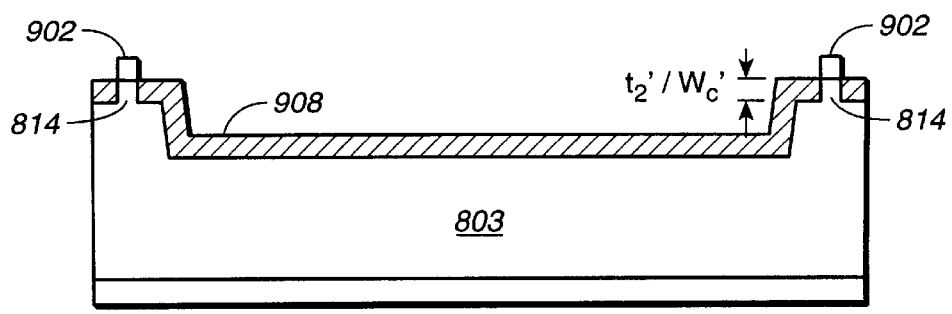
FIG._37
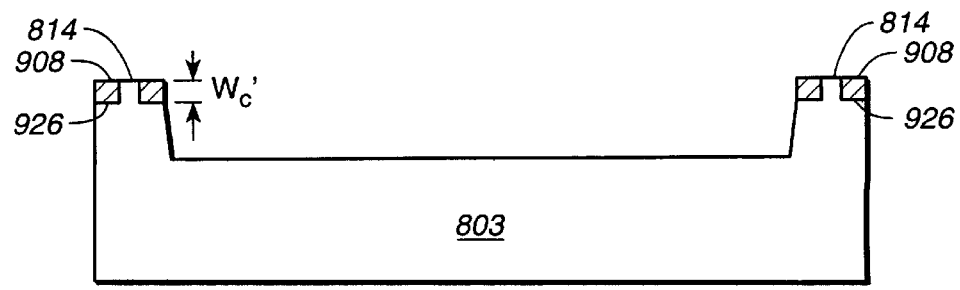
FIG._38

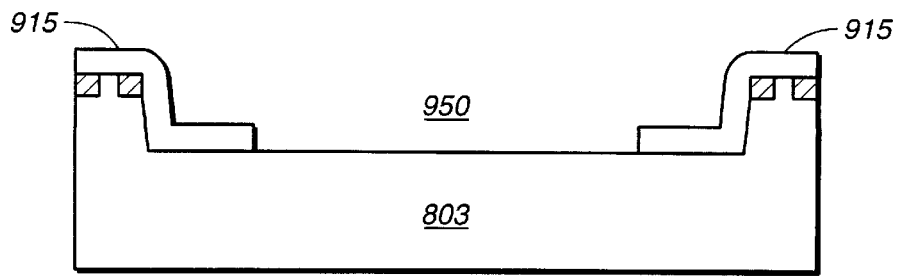
FIG._39
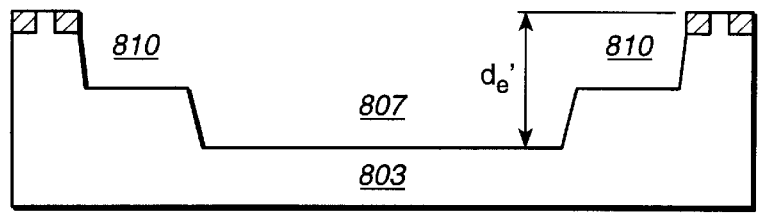
FIG._40
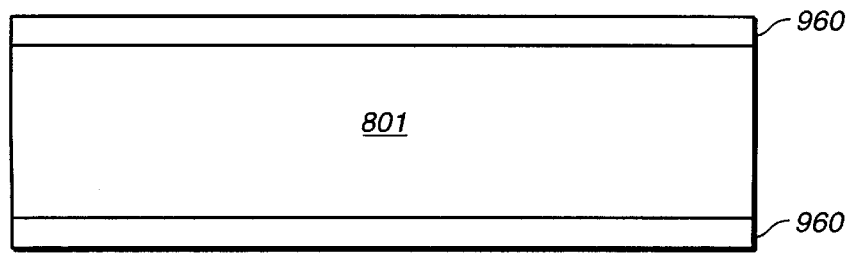
FIG._41
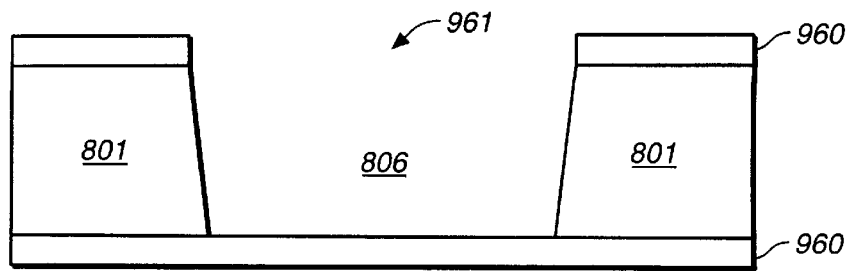
FIG._42

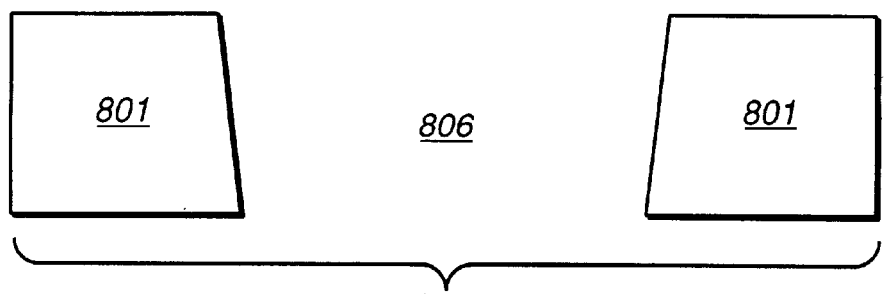
FIG._43
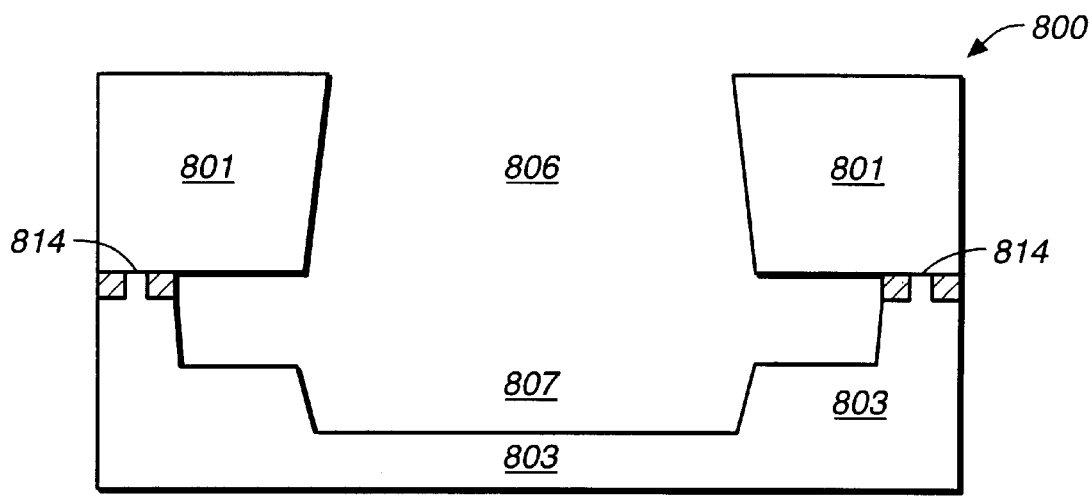
FIG._44
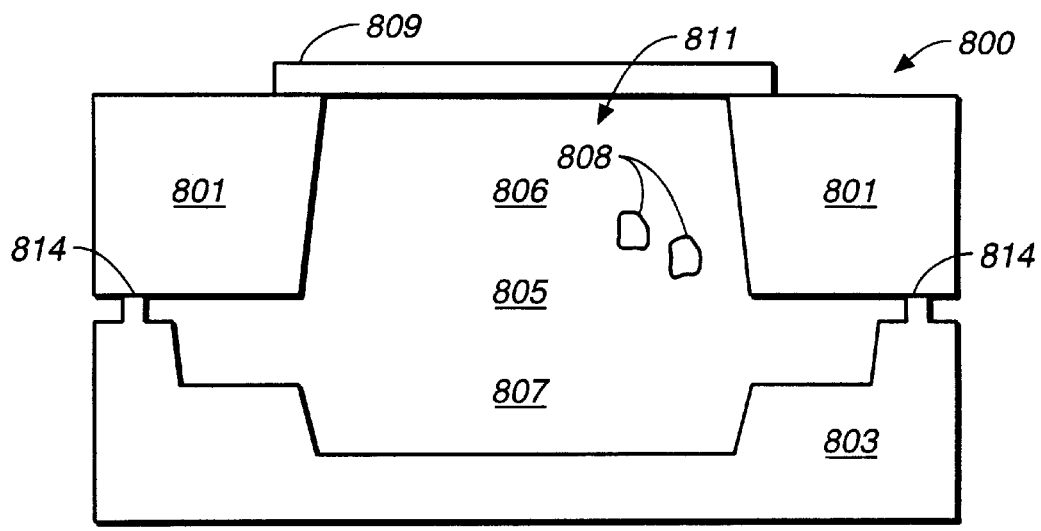
FIG._45

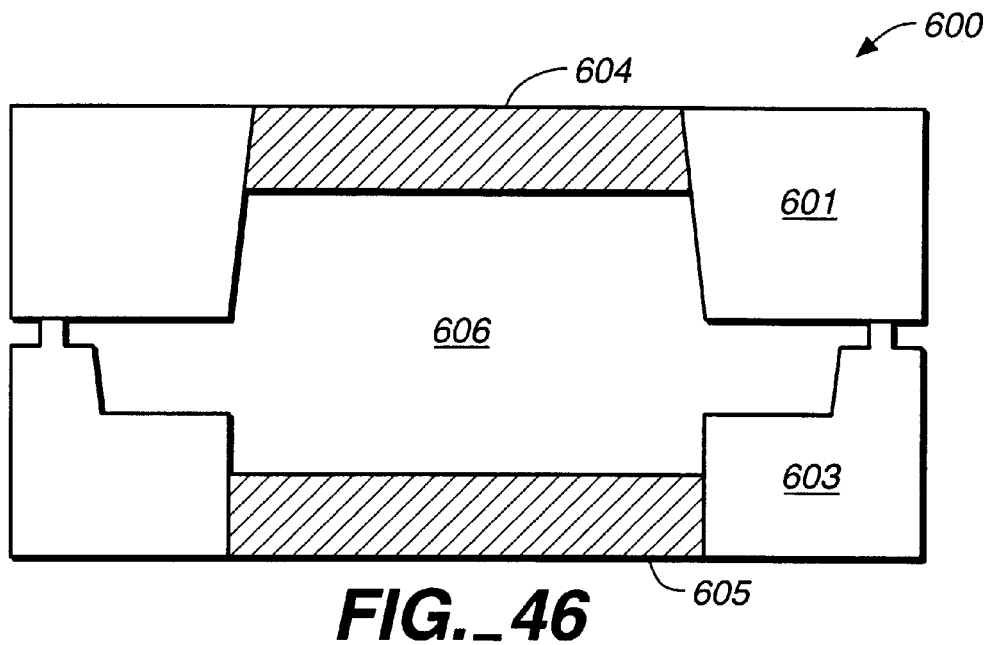
FIG._46
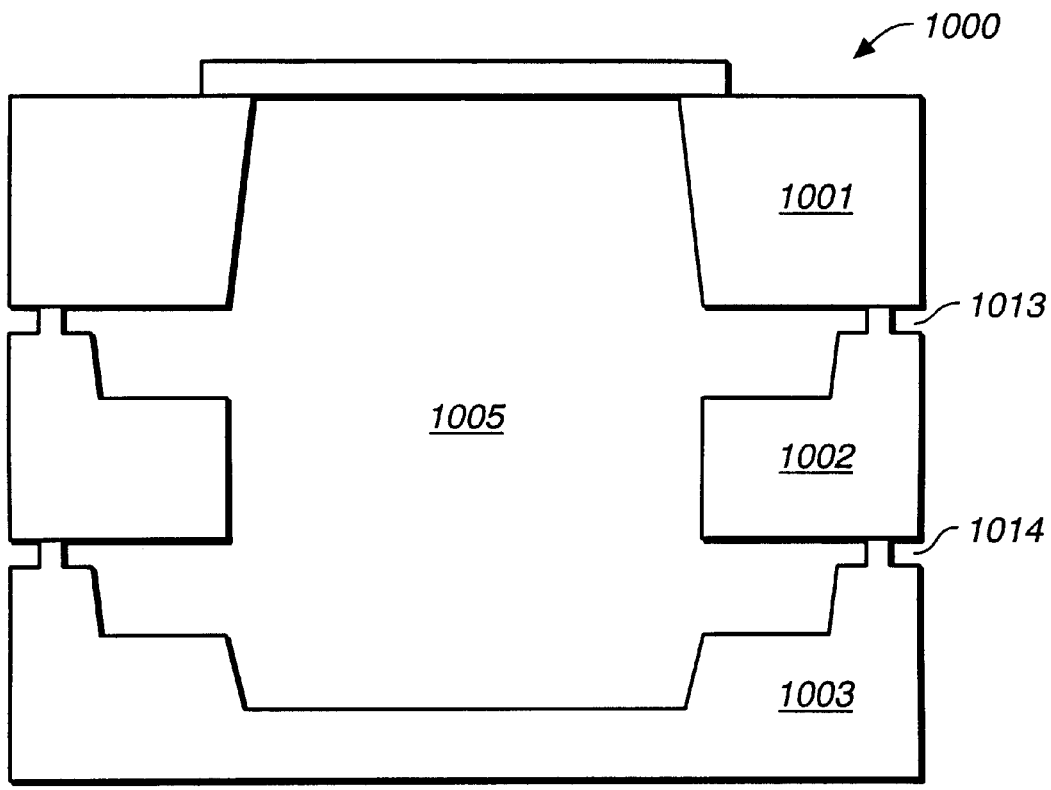
FIG._47

5,938,923

MICROFABRICATED FILTER AND CAPSULE USING A SUBSTRATE SANDWICH

BACKGROUND OF THE INVENTION

The present invention relates generally to filtration devices and more particularly to microfabricated filters constructed with substrate structures. The present invention further relates to containment capsules for immunological isolation of cell transplants that are constructed with substrate structures.

Filtration devices are an indispensable necessity, for example, in the health care industry. Within the health care industry, accurate filtration devices are required, for example, in the fields of pharmaceutical technology, biotechnology, bioseparation, which includes plasma fractionation, and diagnostics. For many applications within these areas, required filtration device features include: precise control of pore size and distribution, absolute pore size as small as the nanometer range, chemical inertness, high mechanical strength, high throughput, and a simple microfabrication process.

Precise control of filter pore sizes down to the 20 nanometer (nm) range would allow biologically important molecules to be mechanically separated on the basis of size. For example, such pore sizes may be used to achieve the heretofore elusive goal of viral elimination from biological fluids. In such absolute filtration applications, the presence of even one unwanted particle could be deleterious.

Microfabricated filters are known in the art to possess such pore sizes. For example, a microfabricated filter comprised of thin film structures is described in co-pending U.S. patent application Ser. No. 08/207,457, entitled "MICROFABRICATED PARTICLE FILTER", filed on Mar. 7, 1994, now U.S. Pat. No. 5,651,900, and assigned to the assignee of the subject application. This filter yields tightly controlled pore sizes and distributions, with a pore width as small as 5 nm. The filtration channels of the filter are entirely composed of polycrystalline silicon (polysilicon).

A microfabricated filter comprised of a combination of substrate and thin film structures is described by Kittilsland et al. in *Sensors and Actuators*, A21–A23 (1990) pp. 904–907. This filter yields a pore width as small as 50 nm. The filtration channels of this filter are composed of a combination of polysilicon and single crystalline silicon.

Another microfabricated filter that is comprised of a combination of substrate and thin film structures is described in co-pending U.S. patent application Ser. No. 08/663,644, entitled "MICROFABRICATED FILTER WITH SPECIALLY CONSTRUCTED CHANNEL WALLS, AND CONTAINMENT WELL AND CAPSULE CONSTRUCTED WITH SUCH FILTERS", filed on Jun. 14, 1996, now U.S. Pat. No. 5,798,042, and assigned to the assignee of the subject application. This filter has a pore width as small as 5 nm. The filtration channels of this filter are also composed of a combination of polysilicon and single crystalline silicon.

A microfabricated filter that is constructed from silicon devices bonded to a glass plate is described by Brody et al. in "A Planar Microfabricated Fluid Filter," *Transducers '95*, 779–782, 1995. The pores of the filter are defined by spaces formed between barriers etched in the silicon devices and the glass plate. The width of the pores are thus determined by the etch rate of silicon. This filter has been demonstrated to remove 16 micrometer ($\mu$m) particles from a fluid.

SUMMARY OF THE INVENTION

In one aspect, the present invention is directed to a microfabricated filter comprised of substrate structures. The filter is comprised of a first substrate structure, a second substrate structure disposed on the first substrate structure, and at least one channel disposed between the first and second substrate structures. A dimension of each channel is defined by depositing and removing a thickness of a sacrificial layer formed on the first substrate structure. The channel forms a pore of the filter.

The channel between the first and second substrate structures need not defined by removal of a portion of an intermediate bonding layer. The channel may have a width less than about 5 nm and a uniformity to within 1 nm. The first and second substrate structures may be composed of single crystalline silicon. The filter may further include at least a first chamber and at least a second chamber. The channel may be disposed between a pair of first and second chambers. At least one anchor point in the channel may connect the first substrate structure to the second substrate structure. The first and second chambers may each include a plurality of fingers. The fingers of the first chamber may be interdigitated with the fingers of the second chamber, wherein the interdigitated fingers define the channel.

In another aspect, the invention is directed to a method of fabricating a microfabricated filter. The method may begin with providing a first substrate, such as a single crystalline silicon substrate. Next, a first chamber is formed in the first substrate. A second chamber is then formed in the first substrate. Next, a channel is formed in the first substrate between the first and second chambers. This step may include forming, and then removing, a first sacrificial layer from the first substrate. A second substrate may then be provided. Next, at least one opening is formed in the second substrate. Finally, the first and second substrates are bonded such that the opening is aligned with the first chamber.

The method may further include forming a second sacrificial layer in the channel after the formation of the channel. The second sacrificial layer may be removed after the first and second substrates are bonded.

The present invention is further directed to a capsule having a porous region. The capsule is comprised of a first substrate structure having a cavity, a second substrate structure having a cavity and disposed on the first substrate structure, and at least one channel disposed between the first substrate structure and the second substrate structure. The channel is defined by forming a sacrificial layer on the first substrate structure. The channel forms a pore in the porous region having a precisely controlled pore width as small as about 5 nm. The cavities of the first and second substrate structures are aligned to form a capsule chamber, which may be filled with a biologically-active substance. The first and second substrate structures may be composed of single crystalline silicon.

Lastly, the present invention is directed to a method of fabricating such a capsule. The method may begin with providing a first substrate, such as a single crystalline silicon substrate. Next, a channel is formed in the first substrate about a perimeter of the first substrate. This step may include forming, and then removing, a first sacrificial layer from the first substrate. A cavity is then formed in the first substrate interior to the channel. Next, a second substrate is provided. A cavity is then formed in the second substrate. Finally, the first and second substrates are bonded such that the cavity of the first substrate is aligned with the cavity of the second substrate.

The method may further include forming a second sacrificial layer in the channel after the formation of the channel. The second sacrificial layer may be removed after the first and second substrates are bonded.

The filter of the present invention provides the following advantages. First, the filter provides a precisely controlled pore width as small as about 5 nm by using a sacrificial layer to define the pore width. This enables the filter to separate biologically important substances, such as viruses, from a fluid, and is particularly applicable in situations where absolute filtration is required. In the preferred embodiment, the sacrificial layer is composed of silicon dioxide. Using thermal oxidation techniques, a film with very precise and uniform thickness (as uniform as ±3 nm across a 4" wafer) can be grown on the wafer. Another advantage to an oxide film is that, in comparison to a metal film such as aluminum, the oxide film grows conformally and will maintain a uniform thickness even over topological features. Furthermore, an oxide film can be grown pinhole-free down to 5 nm.

Second, the filter provides a relatively high mechanical strength. The filter is constructed solely from single crystalline silicon. Single crystalline silicon has a significantly higher mechanical strength than polysilicon or amorphous silicon. In addition, the filter structure is formed by a channel between two bulk substrates rather than as a free-standing membrane. Also, all the fingers can be accessed through one entry hole. Thus, there is no need to etch numerous holes through the substrate in order to inject fluid into each individual finger. All these factors permit the filtering of fluids under relatively high pressures without breakage of the filter.

Third, the filter can be easily modified to provide a relatively high resistance to the absorption of particles, such as proteins, that may be present in the fluid to be filtered. Single crystalline silicon is more resistant to particle absorption than polysilicon or heavily-boron-doped silicon. This resistance prevents particles from clogging the filter and reducing its throughput. In addition, an oxide is used for the sacrificial layer instead of a metal film, then it can be selectively removed very cleanly without leaving a residue or roughening the surface. This will also lead to lower protein absorption.

Fourth, the filter provides a relatively high throughput due to its relatively large effective filtration area. Throughput may be further increased by as much as 10 to 100 times if the interdigitated finger structure is used. The number and spacing of the fingers is limited only by the lithography, and the spacing could be potentially smaller than 1 $\mu$m.

Fifth, the top wafer is bonded directly to the bottom wafer without an intermediary layer. This direct bonding relaxes the process control requirements. The sacrificial layer can be patterned before bonding. Special photolithographic techniques (such as step coverage over high-aspect ratio features) may be required if patterning is performed after bonding. In addition, the sacrificial layer can be selectively deposited if the correct mask material is chosen. This permits the creation of the anchor points and the channel in the same lithographic step. In addition, if the filter requires further etching or chemical treatment after bonding the top and bottom substrates, the additional processing steps may be performed on the device with fewer precautions. In contrast, further processing of a device with an intermediary bonding layer may lead to bond degradation or feature erosion. Moreover, manufacturers need only concern themselves with the etching selectivity of one material, instead of two or more materials.

Finally, the filter may be fabricated using relatively simple fabrication techniques.

The capsule of the present invention provides advantages similar to those provided by the filter.

Other advantages and features of the present invention will become apparent from the following description, including the claims and drawings.

BRIEF DESCRIPTION OF THE DRAWINGS

The accompanying drawings, which are incorporated in and constitute a part of the specification, schematically illustrate representative embodiments of the present invention and, together with the general description given above and the detailed description of the representative embodiment given below, serve to explain the principles of the present invention.

FIG. 1 is a cross-sectional side view of a filter in accordance with the present invention.

FIG. 2 is a cross-sectional top view of the filter of FIG. 1 along lines 2—2.

FIG. 3 is a top plan view of the filter of FIG. 1.

FIG. 4 is a cross-sectional side view of a filter in accordance with an alternative embodiment of the present invention.

FIG. 5 is a cross-sectional side view of a filter in accordance with another alternative embodiment of the present invention.

FIG. 6A is a cross-sectional top view of the filter of FIG. 5 along lines 6—6.

FIG. 6B is a cross-sectional top view of the filter in accordance with another alternative embodiment of the present invention.

FIG. 7 is a cross-sectional side view of a filter in accordance with yet another alternative embodiment of the present invention.

FIG. 8 is a cross-sectional side view of a filter in accordance with a further alternative embodiment of the present invention.

FIG. 9 is a cross-sectional side view of a mechanical support and tubes attached to a filter in accordance with the present invention.

FIGS. 10–26 are views illustrating steps in the fabrication of the filter of FIG. 1.

FIG. 27 is a cross-sectional side view of a capsule in accordance with the present invention.

FIG. 28 is a cross-sectional top view of the capsule of FIG. 27 along lines 28—28.

FIGS. 29–45 are views illustrating steps in the fabrication of the capsule of FIG. 27.

FIG. 46 is a cross-sectional side view of a capsule in accordance with an alternative embodiment of the present invention.

FIG. 47 is a cross-sectional side view of a capsule in accordance with another alternative embodiment of the present invention.

DESCRIPTION OF THE PREFERRED EMBODIMENTS

FIGS. 1, 2 and 3 illustrate a microfabricated filter 100 in accordance with the present invention. Filter 100 is composed of a top substrate 101 and a bottom substrate 103. Top substrate 101 and bottom substrate 103 are composed of a single crystalline material, such as single crystalline silicon. Filter 100 includes one or more filtration structures 120. Filtration structure 120 may be large enough to encompass the entire substrate. Alternatively, filtration structure 120 may be relatively small and be replicated many times across the substrate.

Filtration structure 120 includes anchor regions 119 and anchor points 114 where top substrate 101 is joined to bottom substrate 103. Filtration structure 120 also includes an entry port 105 and an exit port 107 in top substrate 101. Entry port 105 provides a means for supplying fluid to filtration structure 120. Exit port 107 provides a means for removing fluid from filtration structure 120. Fluid flows through filtration structure 120 in the direction indicated by arrows 108, or in the opposite direction.

Filtration structure 120 additionally includes an entry flow chamber 109 and an exit flow chamber 111 in bottom substrate 103. Entry flow chamber 109 is generally aligned with entry port 105 to receive fluid from the entry port. Exit flow chamber 111 is generally aligned with exit port 107 to provide fluid to the exit port. Alternatively, entry and exit flow chambers 109 and 111 may be offset from entry and exit ports 105 and 107, respectively, and connected to the ports by means of channels (not shown).

Entry flow chamber 109 and exit flow chamber 111 each have a depth $d_e$, a length $l_e$ and a width $w_e$. If filter 100 is comprised of a single filtration unit 120, length $l_e$ may be a substantial fraction of the diameter of the substrate, e.g., 150 millimeters (mm) for a 250 mm substrate. Alternatively, if filter 100 is comprised of multiple filtration units 120 replicated across the substrate, length $l_e$ may be much smaller, e.g., 8 mm. Depth $d_e$ may be about 5 to 10 $\mu$m. Width $w_e$ may be about 1 mm.

Filtration structure 120 further includes a channel 113 defined by a space between top substrate 101 and bottom substrate 103, and between entry flow chamber 109 and exit flow chamber 111. Channel 113 defines the "pore" of filtration structure 120. Channel 113 has a width $w_c$, a length $l_c$ and a depth $d_c$. The width $w_c$, which defines the size of the largest particle that can pass through the channel, may be range from about 5 to 500 nm, and preferably between about 5 and 20 nm. The depth $d_c$ affects the throughput of filtration structure 120 and thus is usually minimized. The depth $d_c$ may be about 1 to 10 $\mu$m. The length $l_c$ also affects the throughput of filtration structure 120, since pore area depends on $l_c$, and thus is usually maximized. For filtration structure 120, in which channel 113 is linear, channel length $l_c$ is equal to entry and exit flow chamber length $l_e$.

Anchor points 114 may be disposed within channel 113. The function of the anchor points is to maintain the separation of top substrate 101 and bottom substrate 103 in channel 113.

Referring back to FIG. 1, in a usual application, fluid to be filtered enters filter 100 through entry port 105. Only certain particles of this fluid, those with maximum dimensions less than the width $w_c$ of channel 113, pass through the channel to exit flow chamber 111. The fluid then exits the filter through exit port 107. The fluid flow through the filter is indicated by arrows 108, although the fluid flow may also occur in a direction opposite to that of arrows 108.

FIG. 4 illustrates an alternative filtration structure 125 with an exit port 116 included in bottom substrate 103 rather than in top substrate 101. With this arrangement, fluid flows through filtration structure 125 in a straight line, as indicated by arrows 108.

FIGS. 5 and 6A illustrate an alternative filtration structure 130 having fingers 110 and 112. Entry flow chamber 109 includes fingers 110 disposed along the edge of the entry flow chamber adjacent to channel 113. Likewise, exit flow chamber 111 includes fingers 112 disposed along the edge of the exit flow chamber adjacent to channel 113. Fingers 110 and 112 are interdigitated to define a serpentine-shaped region that forms channel 113. Fluid enters channel 113 through fingers 110 and exits the channel through fingers 112. Fingers 110 and 112 may be rectangular, as shown in FIG. 6A, but are not limited to this shape. Fingers 110 and 112 have a length $l_f$ and a depth $d_f$. Length $l_f$ may be about 8 mm. Depth $d_f$ may be about 1 to 2 $\mu$m.

Fingers 110 and 112 provide channel 113 with a length $l_c$ that can be much larger than the diameter of bottom substrate 103, due to its serpentine-like shape. For instance, length $l_c$ may be about 600 mm. Since the filtering area of channel 113 is equal to the product of length $l_c$ and width $w_c$, the fingers provide filtration structure 130 with a very large active filtering area and thus high throughput. The throughput of filtration structure 130 with fingers 110 and 112 may be as much as 10 to 100 times greater than filtration structure 120 without the fingers. The increase in throughput depends on the length $l_f$ and density of the fingers used. Throughput is also affected by the finger pattern used.

FIG. 6B illustrates another version of filtration structure 130 in which the tips of fingers 110 and 112 are closed by spacer layers 117. As shown, the fluid flow indicated by arrows 108 through the filter does not pass through the tips of the fingers.

FIG. 7 illustrates an alternative filtration structure 140 with a plurality of filtration channels. Top substrate 401 is joined to bottom substrate 403 at anchor regions 429. Top substrate 401 includes entry port 405 and exit port 407. Bottom substrate 403 includes entry flow chamber 409, intermediate flow chambers 425 and 427, and exit flow chamber 411.

Entry flow chamber 409 is connected to intermediate flow chamber 425 through channel 413 having width $w_{c1}$. Similarly, intermediate flow chamber 425 is connected to intermediate flow chamber 427 through channel 423 having width $w_{c2}$. Likewise, intermediate flow chamber 427 is connected to exit flow chamber 411 through channel 433 having width $w_{c3}$. Sequential filtering may be accomplished by a suitable choice of $w_{c1}$, $w_{c2}$ and $w_{c3}$. Usually, the depths are chosen so that $w_{c1} > w_{c2} > w_{c3}$. As a result, particles of successively smaller dimensions are filtered out of a fluid as it passes through channels 413, 423 and 433, with particles only smaller than $w_{c3}$ exiting filtration structure 140.

FIG. 8 illustrates an alternative filtration structure 150 where channel 513 is disposed in-line with the liquid flow. The in-line positioning of channel 513 improves the throughput of fluid through the filtration structure. In this embodiment, top substrate 501 includes an entry port 505, an exit port 507 and a mesa 555. Top substrate 501 is bonded to bottom substrate 503 such that mesa 555 is substantially coincident with a cavity 557 in bottom substrate 503. The volume between mesa 555 and cavity 557 is comprised of entry flow chamber 509, channel 513 having a depth $w_{c4}$, and exit flow chamber 511.

FIG. 9 illustrates the coupling of tubes 560 and 561 to entry port 105 and exit port 107, respectively, of filter 100. Tubes 560 and 561, respectively, supplies and removes fluid from filter 100.

Also referring to FIG. 9, filter 100 may be supported between plates 562 and 563. These plates may be made of stainless steel. Plates 562 and 563 may be held together using numerous mounting methods, including bolts 564 and 565. Plates 562 and 563 provide filter 100 with increased mechanical strength to prevent the separation or breakage of top substrate 101 and bottom substrate 103.

Fabrication of filtration structures 120, 125, 130, 140, and 150 is comprised of three basic steps: bottom substrate processing, top substrate processing and bonding. The fabrication process will be described specifically for filtration structure 130, although a similar process may be used for the other filtration structures.

Referring to FIG. 10, bottom substrate processing may begin with bottom substrate 103, which may be a single crystalline silicon substrate. A <100>-substrate may be used if tapered sides are desired for entry flow chamber 109 and exit flow chamber 111, as shown in FIG. 1. Alternatively, a <110>-substrate may be used if vertical sides are desired.

Also referring to FIG. 10, a mask layer 201 is then deposited on both surfaces of bottom substrate 103. The mask layer may be composed of low-temperature oxide (LTO). The mask layer may be deposited using low-pressure chemical vapor deposition (LPCVD) at 450° C. for 100 minutes, annealing the layer in nitrogen ($N_2$) gas at 1000° C. for 1 hour. This process forms a layer 1.4 $\mu$m thick.

Next, still referring to FIG. 10, mask layer 201 is photolithographically defined and etched to form openings 250 and 251 that defines entry flow chamber 109 and exit flow chamber 111, respectively. The etch may be performed using reactive ion etching (RIE) by flowing the gases silane ($CF_4$), trifluromethane ($CHF_3$) and helium (He) at 90 sccm, 30 sccm and 120 sccm, respectively, and applying a power of 800 Watts (W), a pressure of 2.8 Torr (T), a frequency of 13.56 Megahertz (MHz).

Referring to FIG. 11, bottom substrate 103 is then etched to form entry flow chamber 109 and exit flow chamber 111. For example, a wet silicon etch may be performed using a solution of 1000 grams (g) of potassium hydroxide (KOH) and 2000 milliliters (ml) of water ($H_2O$) at 75° C. This process forms entry and exit flow chambers having a depth $d_e$ of about 1 to 2 $\mu$m.

Next, referring to FIG. 12, mask layer 201 is removed from bottom substrate 103 using a 5:1 solution of buffered HF acid. A new mask layer 217 is then deposited on the top and bottom surfaces of bottom substrate 103 using LPCVD.

Referring to FIGS. 12 and 13, mask layer 217 is photolithographically defined and etched to form openings 252 and 253 that defines fingers 110 and 112, respectively. Openings 252 and 253 may be arranged in an interdigitated pattern as shown. The etch may be performed using RIE by flowing the gases $CF_4$, $CHF_3$ and He at 90 sccm, 30 sccm and 120 sccm, respectively, and applying a power of 800 W, a pressure of 2.8 T, and a frequency of 13.56 MHz.

Still referring to FIGS. 12 and 13, bottom substrate 103 is then etched to form fingers 110 and 112. Fingers 110 and 112 may be interdigitated as shown, but are not limited to this pattern. The fingers may be formed with a wet silicon etch using a solution of 1000 g of KOH, 2000 ml of $H_2O$, at 75° C. This process forms fingers 110 and 112 having a depth $d_f$ of about 2.

A channel region 115 is formed in the area between fingers 110 and 112. Channel region 115 is used in a subsequent process step to form channel 113 of filtration structure 130. The spacing $l_s$ between the tips of the fingers and the chambers may be about 500 $\mu$m so that "turn-around" portions 121 of channel 115 are wider than "straight-away" portions 123. The spacer layers will be formed on turn-around portions 121.

Referring to FIG. 14, mask layer 217 is then removed using a 5:1 solution of buffered HF. Another mask layer 218 is then deposited for use in defining the anchor points and spacer layers. Mask layer 218 may be LTO or silicon nitride. If silicon nitride is used for mask layer 218, a thin oxide pad layer (~200 Å) is first deposited using thermal oxidation (900° C. for 45 minutes). The silicon nitride can be 2000 Å thick and deposited using LPCVD at a temperature of 835° C. and a pressure of 300 mTorr for 45 minutes. After lithography, mask layer 218 is selectively etched using a reactive ion etch step to define anchor points 114 and spacer layers 117. The plasma for the reactive ion etch step consists of the gases helium (He) and sulfur hexaflouride ($SF_6$) at a ratio of 175 sccm and 50 sccm, respectively, a pressure of 375 mTorr, and a power of 150 W. After the etch step, the underlying pad oxide is stripped using 5:1 buffered HF.

Anchor points 114 are spaced such that the top substrate will not pinch off the channel after bonding. They can be spaced as far apart as 1 mm or as close together as 5 $\mu$m.

Spacer layers 117 are placed at turn-around regions 121 between the ends of the fingers and the entry or exit flow chambers. These layers serve as anchor regions and prevent fluid flow from crossing the finger tips to the opposite flow chamber. Spacer layers 117 also minimize alignment difficulties during the bonding process. Spacer layers 117 allow up to 1 mm misalignment of the top wafer entry port to the entry flow chamber without danger of shunting the fluid flow directly into the fingers.

Next, referring to FIG. 15, a sacrificial layer 203 with thickness t is grown on bottom substrate 103 using a thin film deposition process such as thermal oxidation. Because the nitride or LTO of mask layer 218 slows or inhibits the growth of thermal oxides, only the unmasked regions will see substantial film growth. During the formation of sacrificial layer 203, the process consumes substrate material, e.g., silicon, from channel region 115. As a result, the surface of the channel region is lowered with respect to the rest of bottom substrate 103 including anchor points 114, thereby defining width $w_c$ of channel 113.

Width $w_c$ is related to thickness t of sacrificial layer 203 by the relationship:

$t=2.27 \times w_c$.

For example, for a width $w_c$ of 20 nm, thickness t of sacrificial layer 203 should be 45.4 nm. A sacrificial layer of this thickness may be formed on bottom substrate 103 using a dry oxidation step at 1000° C. for 37 minutes.

The thin film deposition process provides sacrificial layer 203 with a precisely controlled thickness t. Under typical processing conditions, thickness t may vary 3 percent or less over bottom substrate 103. As a result, width $w_c$ may be controlled to within about 1 to 5 nm of the desired width.

Finally, referring to FIG. 16, mask layer 218 and sacrificial layer 203 are removed from bottom substrate 103. The layers may be removed using a solution of concentrated HF acid. The finished bottom substrate 103 has a non-planar top surface.

Alternatively, bottom substrate 103 may be planarized using a sacrificial layer. A planar surface may provide improved contact between bottom substrate 103 and top substrate 101 during the subsequent bonding of the substrates, thereby minimizing the formation of voids in the bond. To planarize bottom substrate 103, the steps illustrated by FIGS. 15 and 16 are replaced by the steps illustrated by FIGS. 17–20. Mask layer 218 should be silicon nitride in this alternate approach. Spacer layers 117 are not illustrated in this alternate approach.

Referring to FIG. 17, a sacrificial layer 207 of thickness $t_1$ is grown on bottom substrate 103 using a thin film deposition process such as thermal oxidation. During the formation of sacrificial layer 207, the process consumes substrate material, e.g., silicon, from channel region 115. As a result, the surface of the channel region is lowered with respect to the rest of bottom substrate 103 including anchor points 114.

The width $w_c$ of channel 113 is related to thickness $t_1$ of sacrificial layer 207 by the relationship:

$t_1 = 1.27 \times w_c$.

For example, for a width $w_c$ of 20 nm, thickness $t_1$ of sacrificial layer 207 should be 25.4 nm. A sacrificial layer of this thickness may be formed on bottom substrate 103 using a dry oxidation step at 950° C. for 40 minutes.

Referring to FIG. 18, sacrificial layer 207 is then removed from bottom substrate 103. A mask may be used for this step to prevent removal of mask layer 218. Sacrificial layer 207 may be removed using a 5:1 solution of buffered HF acid.

Next, referring to FIG. 19, a sacrificial layer 208 is grown on bottom substrate 103 using a thin film deposition process such as thermal oxidation. The formation of sacrificial layer 208, as with sacrificial layer 207, lowers the surface of channel region 115 with respect to the rest of bottom substrate 103. Combined, sacrificial layers 207 and 208 lower channel region 115 by a total amount $w_c$ to form channel 113.

A thickness $t_2$ of sacrificial layer 208 should equal the desired width $w_c$ of channel 113 to make the surface of the sacrificial layer flush with the surface of bottom substrate 103. For example, for a width $w_c$ of 20 nm, thickness $t_2$ of sacrificial layer 208 should also be 20 nm. A silicon dioxide layer of such thickness may be formed using dry oxidation at 950° C. for 40 minutes.

The thin film deposition process provides sacrificial layer 207 and 208 with precisely controlled thicknesses $t_1$ and $t_2$. Under typical processing conditions, thicknesses $t_1$ and $t_2$ may vary 3 percent or less over bottom substrate 103. As a result, width $w_c$ may be controlled to within about 1 to 5 nm of the desired width.

Referring to FIG. 20, if the exit port will not be formed in the bottom substrate, then mask layer 218 is selectively etched using a 85% phosphoric acid bath heated to 160° C. for about 9 hours. The nitride pad oxide is removed using a 25:1 HF dip. Bottom substrate 103 is thus provided with a planar surface.

On the other hand, if the exit port will be formed in the bottom substrate, then mask layer 218 is left intact and a second nitridization step is performed to cover any unexposed areas. This film deposition can be done using LPCVD to produce a 4000 Å thick layer. Openings in the nitride are photolithographically defined and etched down to the underlying silicon surface using a He:SF$_6$ reactive ion etch at 250 W.

Alternatively, for the structure in FIG. 16, only a mask layer such as LTO need be deposited. Openings are defined using photolithography and a reactive ion etch step.

For filtration structure 125 of FIG. 4, the following additional steps are performed on bottom substrate 103 to form exit port 116 in the bottom substrate. Referring to FIG. 21, a protective layer 204 is deposited on both surfaces of bottom substrate 103. Protective layer 204 may be composed of LTO.

Still referring to FIG. 21, opening 205 is then photolithographically defined and etched in protective layer 204. Opening 205 is aligned with exit flow chamber 111 on the opposing side of bottom substrate 103.

Next, referring to FIG. 22, exit port 116 is etched through bottom substrate 103 to reach exit flow chamber 111. This step may comprise a wet etch using ethylene-diamine-pyrocatechol (EDP) at 100° C. for 11 hours.

Still referring to FIG. 22, protective layer 204 is then removed.

Referring to FIG. 23, top substrate processing may begin with top substrate 101, which may be a single crystalline silicon substrate. A <100>-substrate may be used if tapered sides are desired for entry port 105, as shown in FIG. 1. Alternatively, a <110>-substrate may be used if vertical sides are desired.

Also referring to FIG. 23, a protective layer 260 is then deposited on both surfaces of top substrate 101. Protective layer 260 may be composed of phosphosilicate glass (PSG), low-stress silicon nitride, or LTO. An LTO *layer may be formed using LPCVD at 450° C. for 100 minutes, annealing the layer in N$_2$ gas at 1000° C. for 1 hour. This process forms a layer 1.4 µm thick.

Still referring to FIG. 23, openings 261 and 262 are then photolithographically defined and etched in protective layer 260. Opening 261 is positioned such that it will be vertically aligned with entry flow chamber 109 on top substrate 101. Opening 262 is positioned such that it will be vertically aligned with exit flow chamber 111 on bottom substrate 103.

Next, referring to FIG. 24, top substrate 101 is etched completely through to form entry port 105 and exit port 107. This step may be performed with a wet etch using EDP at 100° C. for 11 hours.

Referring to FIG. 25, protective layer 260 is then removed from top substrate 101. Protective layer 260 may be removed using a 5:1 solution of buffered HF acid.

Referring to FIG. 26, processed top substrate 101 is then bonded to processed bottom substrate 103 to form filter 100. Top substrate 101 and bottom substrate 103 are joined such that entry port 105 is generally aligned with entry flow chamber 109. If exit port 107 is located in top substrate 101, the exit port should also be generally aligned with exit flow chamber 111.

Top substrate 101 and bottom substrate 103 are bonded at anchor regions 119 and anchor points 114. The substrates may be bonded using any direct bonding technique that does not introduce a space between the substrates at anchor regions 119 and anchor points 114. For instance, fusion or anodic bonding may be used.

Finally, if bottom substrate 103 includes sacrificial layer 208, filter 100 is placed in an etchant to remove the remaining portion of the sacrificial layer. The etchant may an oxide etchant such as buffered HF acid. This step creates a void where sacrificial layer 208 used to be, thus forming channel 113. Filter 100 may then be rinsed in deionized water to remove residual acid from the substrates. The completed filter 100 is shown in FIG. 1.

An alternative embodiment of the present invention, a microfabricated capsule 800, is shown in FIGS. 27 and 28. The structure of capsule 800 is similar to that of filter 100, except that fluid flow occurs through its sides rather than through its top or bottom.

Capsule 800 includes a top substrate 801 and a bottom substrate 803 enclosing a chamber 805. Top substrate 801 and bottom substrate 803 may be made of single crystalline silicon. Top substrate 801 is bonded to bottom substrate 803 at anchor points 814. Chamber 805 is comprised of a top cavity 806 in top substrate 801 and a bottom cavity 807 in bottom substrate 803. Top substrate 801 may include an opening 811 that is covered by a lid 809. Top cavity 806 and bottom cavity 807 may each have a diameter $w_e'$ of about 6 mm and a depth $d_e'$ of about 400 to 500 µm.

Capsule 800 further includes a channel 813 defined by a space between top substrate 801 and bottom substrate 803, and disposed about the perimeter of chamber 805. Channel 813 defines the "pore" of capsule 800 that allows the controlled flow of substances 808 contained within chamber 805 to the exterior of the capsule. Channel 813 has a width $w_c'$, a length $l_c'$ and a depth $d_c'$. The width $w_c'$, which defines the size of the largest particle that can pass through the channel, may range from about 5 to 500 nm, and preferably between about 5 and 20 nm. The depth $d_c'$ affects the rate at which fluid may pass through capsule 800 and thus is usually minimized. The depth $d_c'$ may be about 1 to 10 μm. The length $l_c'$ also affects this rate, since pore area depends on $l_c'$, and thus is usually maximized.

Still referring to FIGS. 27 and 28, chamber 805 may include projections 810 disposed about its perimeter. As a result, channel 813 is formed along the perimeter of projections 810 in a serpentine-like shape. Fluid enters and exits capsule 800 by passing through projections 810. Projections 810 may project radially from the center of the chamber as shown in FIG. 28, but are not limited to this pattern. Projections 810 have a length $l_f'$ and a depth $d_f'$. Length $l_f'$ may be about 1 mm. Depth $d_f'$ may be about 1 to 2 μm.

Projections 810 provide channel 813 with a length $l_c'$ that can be significantly larger than without the projections due to its non-linear shape. Since the filtering area of channel 813 is equal to the product of length $l_c'$ and width $w_c'$, the projections provide capsule 800 with a very large active filtering area and thus high throughput. The throughput of capsule 800 with projections 810 may be as much as 10 to 100 times greater than a capsule without such projections. The increase in throughput depends on the length $l_f'$ and density of the projections used. Throughput is also affected by the finger pattern used.

Still referring to FIGS. 27 and 28, in a usual application, a substance 808 is disposed in chamber 805 through opening 811. For instance, substance 808 may be a cell, tissue or pharmaceutical composition capable of producing a desired biologically-active molecular product. Capsule 800 may be placed in a host, where a fluid generated by substance 808 may flow out of the capsule into the host. However, only particles with maximum dimensions less than width $w_c'$ of channel 813 may pass into or out of capsule 800. The fluid flow through capsule 800 is indicated by arrows 816, although the fluid flow may also occur in a direction opposite to that of arrows 816.

Fabrication of capsule 800, like filtration structure 120, is comprised of three basic steps: bottom substrate processing, top substrate processing and bonding. Referring to FIG. 29, bottom substrate processing may begin with bottom substrate 803, which may be a single crystalline silicon substrate. A <100>-substrate may be used if tapered sides are desired for bottom cavity 807, as shown in FIG. 27. Alternatively, a <110>-substrate may be used if vertical sides are desired.

Also referring to FIG. 29, a mask layer 901 is then deposited on both surfaces of bottom substrate 803. The mask layer may be composed of LTO. This layer may be formed using LPCVD at 450° C. for 100 minutes, annealing the layer in $N_2$ gas at 1000° C. for 1 hour. This process forms a layer 1.4 μm thick.

Next, referring to FIGS. 29 and 30, mask layer 901 is photolithographically defined and etched to form an opening 815 that defines a subsequently formed recess 809 having projections 810. Openings 818 are also etched in mask layer 901 around the periphery of capsule 800 to define subsequently formed indentations 817 (See FIG. 32).

Referring to FIGS. 31 and 32, bottom substrate 803 is then etched to form recess 809 having projections 810 and indentations 817. This step may be performed using a KOH etch (as before). This process forms recess 809, projections 810 and indentations 817 having a depth $d_f'$ of about 1 to 2 μm.

A channel region 926 is formed in the area between projections 810 and indentations 817. Channel region 926 is used in a subsequent process step to form channel 813 of capsule 800.

Still referring to FIGS. 31 and 32, mask layer 901 is then removed using a 5:1 solution of buffered HF. A new mask layer 902 of silicon nitride or LTO is then deposited. Mask layer 902 is then photolithographically defined and etched to define anchor points 814. Afterwards, the underlying pad oxide is stripped.

Next, referring to FIG. 33, a sacrificial layer 903 is grown on bottom substrate 803 using a thin film deposition process such as thermal oxidation. Because the mask layer 902 slows or inhibits the growth of thermal oxides, only the unmasked regions will see substantial growth. During the formation of sacrificial layer 903, the process consumes substrate material, e.g., silicon, from channel region 926 except for the areas covered by mask layer 902. As a result, the surface of the channel region is lowered with respect to anchor points 814, thereby defining width $w_c'$ of channel 813.

Width $w_c'$ is related to a thickness t' of sacrificial layer 903 by the relationship:

$t' = 2.27 \times w_c'$.

For example, for a width $w_c'$ of 20 nm, thickness t' of sacrificial layer 903 should be 45.4 nm. A sacrificial layer of this thickness may be formed on bottom substrate 803 using a dry oxidation step at 1000° C. for 37 minutes.

The thin film deposition process provides sacrificial layer 903 with a precisely controlled thickness t'. Under typical processing conditions, thickness t' may vary 3 percent or less over bottom substrate 803. As a result, width $w_c'$ may be controlled to within about 1 to 5 nm of the desired width.

Referring to FIG. 34, mask layer 902 and sacrificial layer 903 are then removed from bottom substrate 803. The layers may be removed using a solution of concentrated HF acid. Bottom substrate 803 has a non-planar top surface.

Alternatively, bottom substrate 803 may be planarized using a sacrificial layer. A planar surface may provide improved contact between bottom substrate 803 and top substrate 801 during the subsequent bonding of the substrates, thereby minimizing the formation of voids in the bond. To planarize bottom substrate 803, the steps illustrated by FIGS. 33 and 34 are replaced by the steps illustrated by FIGS. 35–38. The mask layer 902 should be silicon nitride in this alternate approach.

Referring to FIG. 35, a sacrificial layer 907 with a thickness $t_1'$ is grown on bottom substrate 803 using a thin film deposition process such as thermal oxidation. During the formation of sacrificial layer 907, the process consumes substrate material, e.g., silicon, from channel region 926. As a result, the surface of the channel region is lowered with respect to the rest of bottom substrate 803 including anchor points 814.

The width $w_c'$ is related to thickness $t_1'$ of sacrificial layer 907 by the relationship:

$t_1' = 1.27 \times w_c'$.

For example, for a width $w_c'$ of 20 nm, thickness $t_1'$ of sacrificial layer 907 should be 25.4 nm. A sacrificial layer of this thickness may be formed on bottom substrate 803 using a dry oxidation step at 950° C. for 40 minutes.

The thin film deposition process provides sacrificial layer 907 with a precisely controlled thickness $t_1'$. Under typical processing conditions, thickness $t_1'$ may vary 3 percent or less over bottom substrate 103. As a result, width $w_c'$ may be controlled to within about 1 to 5 nm of the desired width.

Referring to FIG. 36, sacrificial layer 907 is then removed from bottom substrate 803. A mask may be used for this step to prevent removal of mask layer 902. Sacrificial layer 907 may be removed using a 5:1 solution of buffered HF acid.

Next, referring to FIG. 37, a sacrificial layer 908 with a thickness $t_2'$ is grown on bottom substrate 803 using a thin film deposition process such as thermal oxidation. The formation of sacrificial layer 908, as with sacrificial layer 907, lowers the surface of channel region 926 with respect to the rest of bottom substrate 803. Combined, sacrificial layers 907 and 908 lower channel region 926 by a total amount $w_c'$ to form channel 813.

Thickness $t_2'$ of sacrificial layer 908 should equal the desired width $w_c'$ of channel 813 to make the surface of the sacrificial layer flush with anchor points 814. For example, for a width $w_c'$ of 20 nm, thickness $t_2'$ of sacrificial layer 908 should also be 20 nm. A silicon dioxide layer of such thickness may be formed by dry oxidation at 950° C. for 40 minutes.

Referring to FIG. 38, mask layer 902 is selectively etched using a 85% phosphoric acid bath heated to 160° C. for about 9 hours. The exposed nitride pad oxide is then removed from bottom substrate 803 using a 25:1 HF dip. A mask may be used for this step to prevent removal of sacrificial layer 908 from channel region 926. Bottom substrate 803 is thus provided with a planar surface.

Next, referring to FIG. 39, a mask layer 915 is deposited on bottom substrate 803. The mask layer is photolithographically defined and etched to form opening 950 that defines bottom cavity 807. Mask layer 915 may be made of polyhexane, a nitride or a polymer.

Referring to FIG. 40, bottom substrate 803 is then etched to form bottom cavity 807. The bottom substrate may be etched using, for instance, EDP at 100° C. for 8 hours, producing bottom cavity 807 having a depth $d_e'$ of about 400 μm. Alternatively, a plasma etch or $XeF_2$ etch may be used.

Finally, still referring to FIG. 40, mask layer 915 is removed from bottom substrate 803. The mask layer may be removed using a 5:1 solution of buffered HF acid.

Referring to FIG. 41, top substrate processing may begin with top substrate 801, which may be a single crystalline silicon substrate. A <100>-substrate may be used if tapered sides are desired for top cavity 806, as shown in FIG. 27. Alternatively, a <110>-substrate may be used if vertical sides are desired.

Next, still referring to FIG. 41, a mask layer 960 is deposited on both surfaces of top substrate 801. Mask layer 960 may be composed of LTO or PSG. This layer may be formed using LPCVD at 450° C. for 100 minutes, annealing the layer in $N_2$ gas at 1000° C. for 1 hour. This process forms a layer 1.4 μm thick.

Referring to FIG. 42, mask layer 960 is then photolithographically defined and etched to form an opening 961 that defines top cavity 806.

Next, still referring to FIG. 42, top substrate 801 is then etched completely through to form top cavity 806 and opening 811. The etch may be performed using a wet etch using EDP at 100° C. for 11 hours.

Referring to FIG. 43, mask layer 960 is then removed from top substrate 801. The mask layer may be removed using a 5:1 solution of buffered HF acid.

Referring to FIG. 44, top substrate 801 is then turned over and bonded to bottom substrate 803 to form capsule 800. Top substrate 801 and bottom substrate 803 are joined such that top cavity 806 is generally aligned with bottom cavity 807. Top substrate 801 and bottom substrate 803 may be bonded at anchor points 814. The substrates may be bonded using any direct bonding technique that does not introduce a space between the substrates at anchor points 814. For instance, direct or anodic bonding may be used.

Next, if bottom substrate 803 includes sacrificial layer 908, capsule 800 may be placed in an etchant, such as an oxide etchant, to remove the remaining portion of sacrificial layer 908. The oxide etchant may be buffered HF acid. This step creates a void where sacrificial layer 908 used to be, thus forming channel 813. Capsule 800 may then be rinsed in deionized water to remove residual acid from the substrates.

Referring to FIG. 45, substance 808 may then be placed in chamber 805 through opening 811 in top substrate 801. Finally, lid 809 may be placed on opening 811 to seal capsule 800. The lid may be fastened to the capsule using an epoxy adhesive.

Other embodiments of capsules in accordance with the present invention are possible. Referring to FIG. 46, a capsule 600 may include a top substrate 601 and a bottom substrate 603 having microfabricated filter structures 604 and 605, respectively. By including such structures, fluid flow into or out of a chamber 606 of capsule 600 occurs not only through its sides, but also through its top and bottom. Microfabricated filter structures 601 may be composed of substrate and thin film structures as described in the above-mentioned U.S. patent application Ser. No. 08/663,644, now U.S. Pat. No. 5,798,042 which is incorporated herein by reference.

Referring to FIG. 47, a capsule 1000 may be formed by stacking more than two substrates on top of each other, such as substrates 1001, 1002 and 1003. By stacking multiple substrates, the volume of a chamber 1005 in capsule 1000 is increased. Also, liquid flow into or out of capsule 1000 is increased due to multiple channels 1013 and 1014.

The filters and capsules of the present invention are created without an intermediate bonding layer. This provides several benefits as the use of an intermediary layer as both a bonding layer and a channel width determinant can present several problems. When removing the intermediary layer after bonding, the etch must be carefully controlled or the intermediary layer will be over-etched and the bonding will be weakened. Also, if a metal film is used, it is more difficult to deposit pinhole-free films of very small thicknesses (200–500 A). This could led to overstretching problems when removing the intermediary layer. In addition, deposition of metal films by evaporation or sputtering can affect the thickness uniformity. In evaporation and sputtering techniques, topological features on the surface (such as mesas or trenches) produce different deposition rates than a flat surface. This thickness variation will be significantly larger than ±3 nm across a 4" wafer. In addition, proteins tend to absorb on rougher surfaces. If the post-bonding etching is not adequately controlled, then the surface can be roughened and thus lead to higher protein absorption. Also, if the filter undergoes any high-temperature processing after bonding, it is possible the intermediary layer could reflow, resulting in a change in the channel thickness.

In addition, the filters of the present invention are formed by channels between the bulk substrates. This provides several benefits, as bulk etching to expose a filter structure membrane can present problems. First, an exposed membrane is less mechanically stable than a bulk silicon substrate. The lack of mechanical stability could present problems when operating at high pressures. Second, bulk etching of channels for fluid to flow into each finger individually is difficult to perform with standard anisotropic etching or reactive ion etching. In addition, in order to perform bulk etching, the parts that are not to be etched must be first doped heavily with boron. This leads to rougher surfaces and higher protein absorption.

Furthermore, all the feature sizes in the filters and capsules of the present invention are controlled and limited by lithography. Using lithography, the channel distance could be small as 0.25 μm if current technology is used. Similarly, the finger widths could be reduced to this size as well. In this case, instead of using an anisotropic wet etch to form the fingers, a reactive ion etch could be used.

The present invention has been described in terms of representative embodiments. The invention, however, is not limited to the embodiments depicted and described. Rather, the scope of the invention is defined by the appended claims.

What is claimed is:

1. A filter comprising:
   a first substrate structure directly bonded to a second substrate structure; and,
   at least one pore located between the first and second substrate structures having a pore size less than about 500 nm and having a pore uniformity of ±1–3 nm,
   wherein said first substrate structure and second substrate structure each comprise single crystalline silicon.

2. The filter of claim 1, wherein said at least one pore is formed by sacrificing at least one sacrificial layer formed by a thin-film deposition process.

3. The filter of claim 1, wherein said pore size is a width.

4. The filter of claim 1, wherein said pore size is less than about 50 nanometers.

5. The filter of claim 1, wherein said pore size is in the range of about 5–20 nanometers.

6. The filter of claim 1, wherein said pore size is in the range of about 1–5 nanometers and the pore uniformity is about ±1 nm.

7. The filter of claim 1, wherein said pore size is less than about 1 nm and the pore uniformity is ±1 nm.

8. The filter of claim 1, wherein said pore size is about 5 nanometers and the pore uniformity is about ±1 nm.

9. The filter of claim 1, wherein said pore size is about 2 nanometers and the pore uniformity is about ±1 nm.

10. The filter of claim 1, wherein said pore size is about 1 nanometer and the pore uniformity is about ±1 nm.

11. The filter of claim 1, further comprising a plurality of anchor points located proximate to the pores and connecting the first and second substrate structures.

12. The filter of claim 1, wherein the first substrate structure is directly bonded to the second substrate structure by a fusion or anodic bond.

13. The filter of claim 1, wherein the at least one pore is linear and about 8–150 mm in length.

14. The filter of claim 1, wherein the at least one pore is serpentine-shaped and is about 600 mm in length.

15. The filter of claim 1 comprising a plurality of pores.

16. The filter of claim 1 comprising a plurality of pores, wherein at least two of the pores have different pore sizes to sequentially filter a throughput having more than one specie.

17. A method of fabricating a filter comprising the steps of:
   providing a first single crystalline silicon substrate having masked and unmasked portions;
   depositing a first sacrificial layer having a thickness t on said unmasked portions;
   creating a pore width of about t÷2.27±1–5 nm by removing said first sacrificial layer from said first single crystalline substrate forming a recess; and
   directly bonding a second single crystalline silicon substrate to the first crystalline substrate.

18. The method of claim 17 further comprising:
   depositing a second sacrificial layer in said recess to prevent the second substrate from blocking off the pore; and
   removing said second sacrificial layer from said recess.

19. The method of claim 17, wherein the first substrate is directly bonded to the second substrate by a fusion or anodic bond.

20. A capsule having a porous region comprising:
   a first substrate structure having at least one first cavity;
   a second substrate structure having at least one second cavity directly bonded to said first substrate structure, wherein said at least one first and second cavity define at least one chamber;
   at least one pore having a pore size of less than about 500 nm and having a pore uniformity of ±1–3 nm,
   wherein said first and second substrate structures each comprise since crystalline silicon.

21. The capsule of claim 20, further comprising a biologically-active substance disposed within said at least one chamber.

22. The capsule of claim 20, wherein said at least one chamber includes a plurality of projections.

23. The capsule of claim 20, wherein the first substrate structure is directly bonded to the second substrate structure by a fusion or anodic bond.

24. The capsule of claim 20, wherein the at least one pore is linear and about 8–150 mm in length.

25. The capsule of claim 20, wherein the at least one pore is serpentine-shaped and is about 600 mm in length.

26. The capsule of claim 20 comprising a plurality of pores.

27. A method of fabricating a capsule having a porous region comprising the steps of:
   providing a first single crystalline silicon substrate;
   forming a recess in said first single crystalline silicon substrate;
   forming a first cavity in said first single crystalline silicon substrate;
   providing a second single crystalline silicon substrate;
   forming a second cavity in said second single crystalline silicon substrate; and
   directly bonding said first and second single crystalline silicon substrates, wherein the first and second cavities are aligned.

28. The method of claim 27, wherein said forming the recess includes:
   forming a first sacrificial layer on said first single crystalline substrate; and
   removing said first sacrificial layer from said first single crystalline substrate.

29. The method of claim 27 wherein the recess forming act includes the acts of:
   depositing a mask on a portion of the first crystalline substrate to produce masked and unmasked portions;
   depositing a second sacrificial layer having a thickness t on said unmasked portions and
   removing said second sacrificial layer producing the recess having a depth of t divided by about 1.27.

30. The method of claim 27, wherein the first substrate is directly bonded to the second substrate by a fusion or anodic bond.

31. A capsule comprising:
   a plurality of directly bonded single crystalline silicon substrates having a plurality of anchor points each located between the substrates;
   a plurality of chambers each located between the substrates; and,
   a plurality of pores, each located between the substrates, each having a pore size less than about 500 nm, and having a pore uniformity of about ±1–3 nm.

* * * * *

UNITED STATES PATENT AND TRADEMARK OFFICE
CERTIFICATE OF CORRECTION

PATENT NO.    : 5,938,923
DATED         : August 17, 1999
INVENTOR(S)   : Jay Kuang-Jich Tu and Mauro Ferrari It is certified that error appears in the above-identified patent and that said Letters Patent is hereby corrected as shown below:

<u>Column 15, lines 64-67 through Column 16, lines 1-7,</u>
Claim 20, should read:

20. A capsule having a porous region comprising:
a first substrate structure having at least one first cavity;
a second substrate structure having at least one second
   cavity directly bonded to said first substrate structure,
   wherein said at least one first and second cavity define
   at least one chamber;
at least one pore having a pore size of less than about 500
   nm and having a pore uniformity of ±1-3 nm,
wherein said first and second substrate structures each
   comprise single crystalline silicon.

Signed and Sealed this

Twenty-ninth Day of July, 2003

JAMES E. ROGAN
*Director of the United States Patent and Trademark Office*